(12) United States Patent
Van Bogaert et al.

(10) Patent No.: US 9,388,443 B2
(45) Date of Patent: Jul. 12, 2016

(54) **LACTONASE DERIVED FROM *CANDIDA BOMBICOLA* AND USES THEREOF**

(71) Applicant: Universiteit Gent, Ghent (BE)

(72) Inventors: Inge Van Bogaert, Kalken (BE);
Katarzyna Ciesielska, Iowicz (PL);
Bart Devreese, Vosselare (BE); Wim Soetaert, Lovendegem (BE); Sophie Roelants, Ghent (BE)

(73) Assignee: Universiteit Gent, Ghent (BE)

( * ) Notice: Subject to any disclaimer, the term of this patent is extended or adjusted under 35 U.S.C. 154(b) by 16 days.

(21) Appl. No.: 14/363,722

(22) PCT Filed: Dec. 14, 2012

(86) PCT No.: PCT/EP2012/075571
§ 371 (c)(1),
(2) Date: Jun. 6, 2014

(87) PCT Pub. No.: WO2013/092421
PCT Pub. Date: Jun. 27, 2013

(65) Prior Publication Data
US 2014/0335567 A1    Nov. 13, 2014

(30) Foreign Application Priority Data
Dec. 20, 2011 (EP) ..................................... 11194538

(51) Int. Cl.
*C12N 9/18* (2006.01)
*C12P 19/44* (2006.01)

(52) U.S. Cl.
CPC . *C12P 19/44* (2013.01); *C12N 9/18* (2013.01); *C12P 19/445* (2013.01); *C12Y 301/01025* (2013.01); *Y02P 20/52* (2015.11)

(58) Field of Classification Search
CPC ....... C12P 19/44; C12P 19/14; C12N 9/2402; C12Y 301/01025
USPC ............................... 435/197, 190, 254.22, 74
See application file for complete search history.

(56) References Cited

U.S. PATENT DOCUMENTS

2010/0003708 A1    1/2010  Svendsen et al.
2012/0058527 A1    3/2012  Madrid

FOREIGN PATENT DOCUMENTS

JP    2008247845 A    10/2008
WO   2004044216 A1    5/2004
WO   2008040738 A1    4/2008
WO   2010111143 A2    9/2010
WO   2013092421 A1    6/2013

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Van Bogaert et al., Microbial synthesis of sophorolipids, Process Biochemistry, Jan. 11, 2011, pp. 821-33, vol. 46, No. 4.
PCT International Search Report, PCT/EP2012/075571, dated May 22, 2013.
Asmer HJ, Lang S, Wagner F, Wray V (1988) Microbial production, structure elucidation and bioconversion of sophorose lipids. J Am Oil Chem Soc 65: 1460-1466.
Davila AM, Marchal R, Vandecasteele JP (1994) Sophorose lipid production from lipidic precursors—Predictive evaluation of industrial substrates. J Indust Microbiol 13: 249-257.
Davila AM, Marchal R, Vandecasteele JP (1997) Sophorose lipid fermentation with differentiated substrate supply for growth and production phases. Appl Microbiol Biotechnol 47:496-501.
Garcia-Ochoa F, Casas JA (1999) Unstructured kinetic model for sophorolipid production by Candida bombicola. Enzyme Microb Technol 25:613-621.
Hommel RK, Weber L, Weiss A, Himmelreich U, Rilke O, Kleber HP (1994) Production of sophorose lipid by Candida (Torulopsis) apicola grown on glucose. J Biotechnol 33:147-155.
Hu YM, Ju LK (2001b) Sophorolipid production from different lipid precursors observed with LC-MS. Enzyme Microbial Technol 29: 593-601.
Konishi M, Fukuoka T, Morita T, Imura T, Kitamoto D (2008) Production of new types of sophorolipids by Candida bastitae.J Oleo Sci 57: 359-369.
Nunez A, Foglia TA, Ashby R. (2003) Enzymatic synthesis of a galactopyranose sophorolipid fatty acid-ester. Biotechnol Lett 25:1291-1297.
Stüwer O, Hommel R, Haferburg D, Kleber HP (1987) Production of crystalline surface-active glycolipids by a strain of Torulopsis apicola. J Biotechnol 6: 259-269.
Van Bogaert INA, Zhang J, Soetaert W (2011) Microbial synthesis of sophorolipids. Process Biochem 46: 821-833.

* cited by examiner

*Primary Examiner* — Md. Younus Meah
(74) *Attorney, Agent, or Firm* — TraskBritt, P.C.

(57) ABSTRACT

The present disclosure relates to an enzyme derived from *Candida bombicola* that is capable of lactonizing or polymerizing carbohydrate-containing compounds, lipids, fatty acids, hydroxylated fatty acids, alcohols, dicarboxylic acids or mixtures thereof. Hence, host cells comprising the latter enzyme can be used, via the formation of intra- or inter-molecular ester-bounds, to produce, for example, lactonized sophorolipids or polymers of acidic sophorolipids. On the other hand, host cells having lost their capability to produce a functional enzyme disclosed herein can be used to produce 100% acidic sophorolipids.

7 Claims, 15 Drawing Sheets a
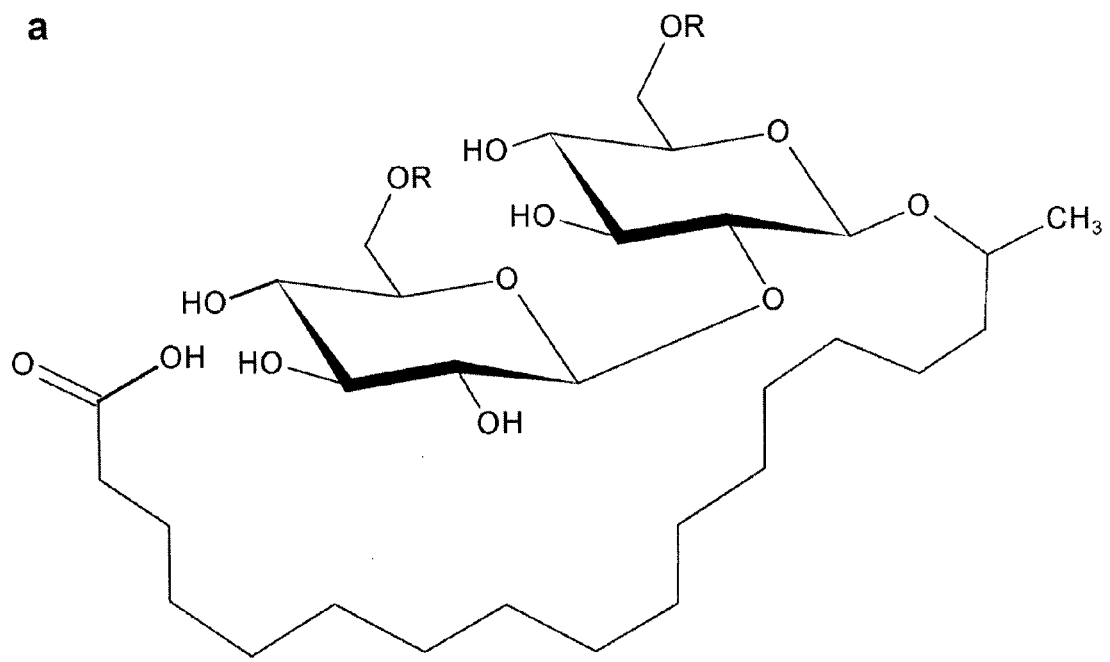
b
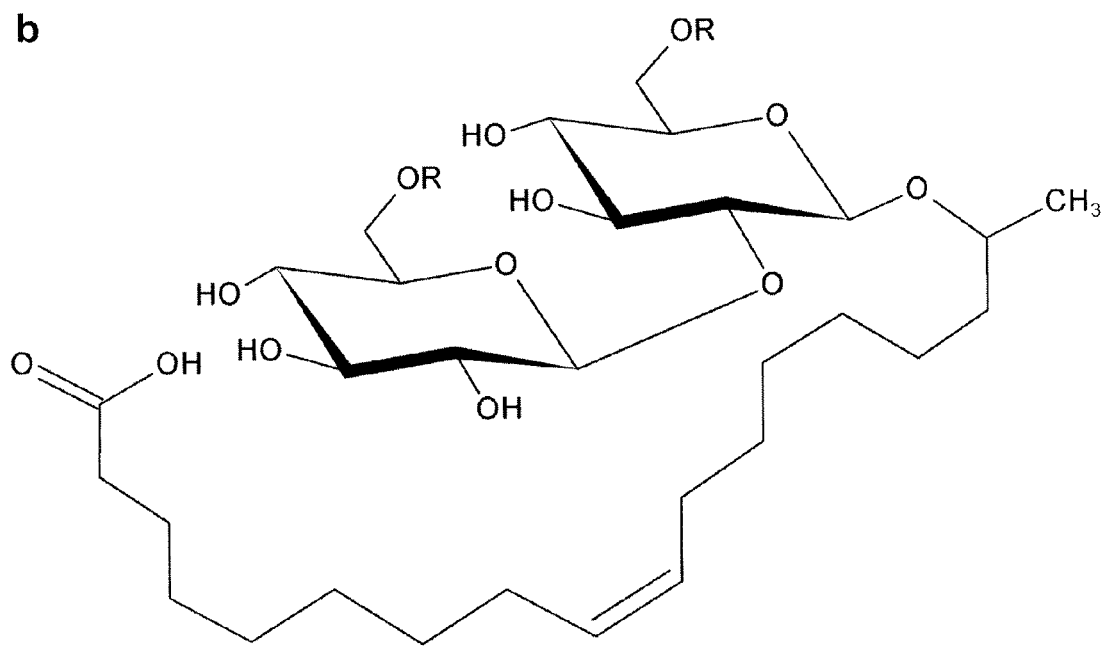
FIG. 1

Sophorolipids are considered to be a mixture of compounds represented by formulas (a) acidic form or (b) lactonic form $R_1$ = -H or -C(O)CH$_3$ $R_2$ = -H or -C(O)CH$_3$ $R_3$ = saturated or unsaturated hydrocarbon chain with m carbon atoms $R_4$ = saturated or unsaturated hydrocarbon chain with n carbon atoms $R_5$ = -COOH, -CH$_2$(R$_6$) or -CH(R$_6$)CH$_3$ $R_6$ = -H, -OH or OR$_7$ in which (m+n) >1 and <26 and m and n are independently of one another >=0 and <26

(a)
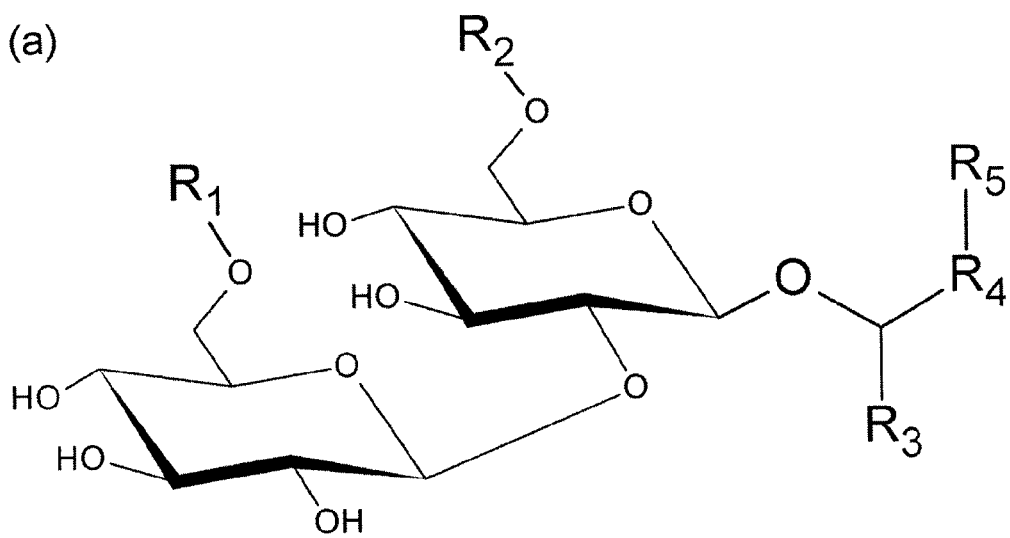

$R_7$ =
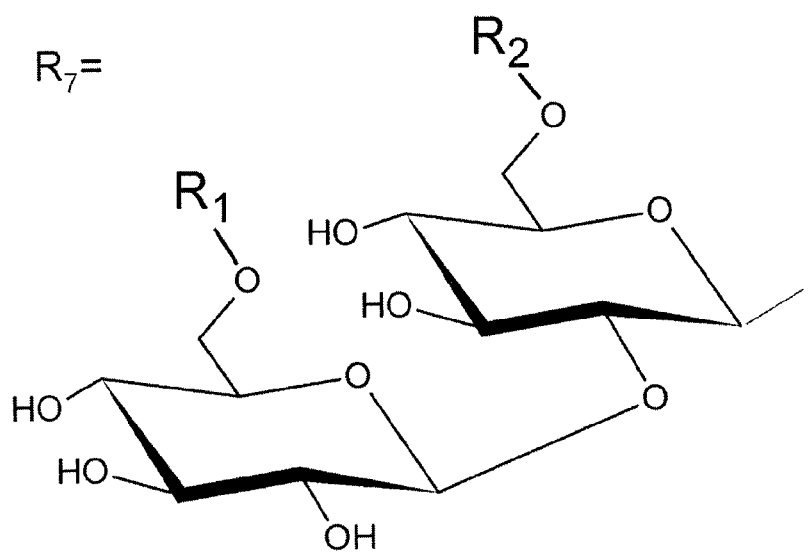

FIG. 2A

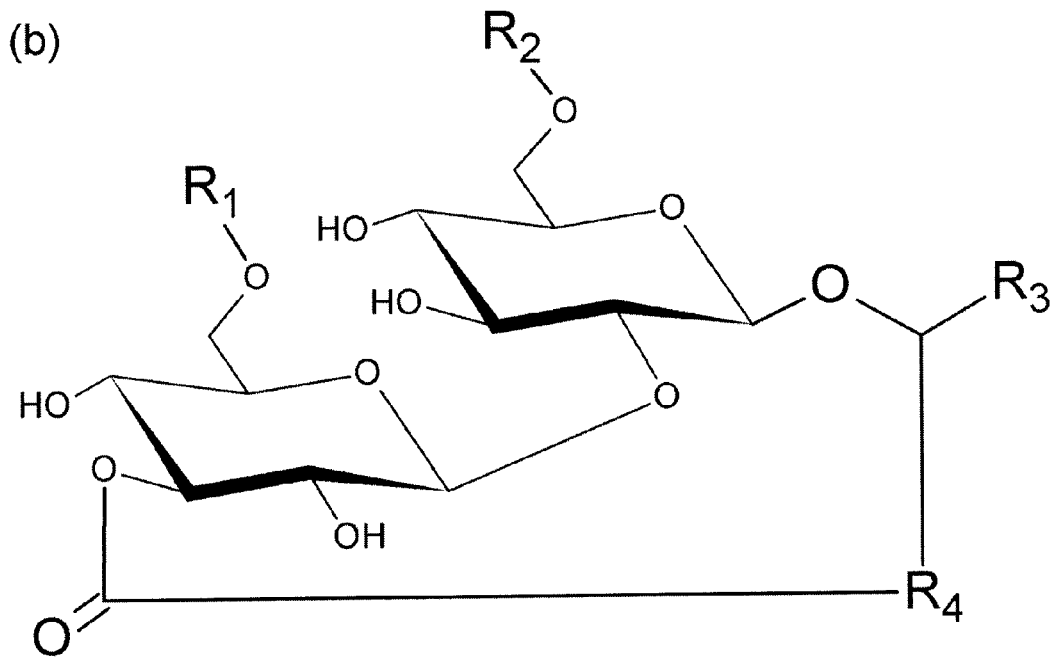

FIG. 2B

```
                                                              Seq ID N° 29
  1   MLALFFSLAP  LLSQALPLGY  TAAPAESFYF  WPENISSLQA  GEIFRKRELL
          Seq ID N° 28
 51   TLPDIFDFGP  NLEKVVQVAY  KTRLTDGNDS  FSIASIFIPK  NPSPELKLYS
          Seq ID N° 26-27   Seq ID N° 22                Seq ID N° 21
101   YQTFEDAVQL  DCAPSYALFV  GNKSSNYLPV  TSNLSAISRE  LEKGRHCIIP

151   DHEGYISGFF  AGRQEGYAGL  DGIRAARNYL  NGTNETPIGI  FGYSGGAQAI
                       Seq ID N° 23
201   AWIVDLHDEY  APDLNFVGTV  SGGTLVDAWG  TFQYIDYPKV  YLKGSILIMY

251   TGLFSGYPAQ  FEVIWPYIEP  VIQENMLLLR  LAPNDCNQSP  ILQGYNKSIM

301   AGIHVDLPEF  PASKYIFQHE  SLLANYSVVP  VSTPKFPRYM  YHGGSDELAK
                                                        Seq ID N° 24-25
351   LSLVEQYVDQ  QWNTGANLTF  VVYPGLLHDE  TAYRGFDAAM  DWLDAQLDSG

401   YLPPVNSTHT  (SEQ ID N° 2)
```

FIG. 3

FIG. 4A (upper part)

FIG. 4B (lower part)

FIG. 5A (upper part)

FIG. 5B (lower part)

LACTONASE DERIVED FROM *CANDIDA BOMBICOLA* AND USES THEREOF

CROSS-REFERENCE TO RELATED APPLICATIONS

This application is a national phase entry under 35 U.S.C. §371 of International Patent Application PCT/EP2012/075571, filed Dec. 14, 2012, designating the United States of America and published in English as International Patent Publication WO 2013/092421 A1 on Jun. 27, 2013, which claims the benefit under Article 8 of the Patent Cooperation Treaty and under 35 U.S.C. §119(e) to European Patent Application Serial No. 11194538.2, filed Dec. 20, 2011.

TECHNICAL FIELD

The disclosure relates to an enzyme derived from *Candida bombicola* that is capable of lactonizing or polymerizing carbohydrate-containing compounds, lipids, fatty acids, hydroxylated fatty acids, alcohols, dicarboxylic acids or mixtures thereof. Hence, host cells comprising the latter enzyme can be used, via the formation of intra- or inter-molecular ester-bounds, to produce, for example, lactonized sophorolipids or polymers of acidic sophorolipids. On the other hand, host cells having lost their capability to produce a functional enzyme of the present disclosure can be used to produce 100% acidic sophorolipids.

BACKGROUND

The non-pathogenic yeast *Candida* (*Starmerella*) *bombicola* ATCC 22214 (CBS 6009) is commercially applied for the production of sophorolipids. These glycolipid biosurfactants are constituted of a sophorose head group (2-O-β-D-glucopyranosyl-D-glucopyranose) attached to a (sub)terminal hydroxylated $C_{18}$ or $C_{16}$ fatty acid by a glycosidic linkage between the anomeric C-atom of the sugar and the hydroxyl group of the fatty acid. Sophorolipids are typically produced by fermentation in the presence of a hydrophobic carbon source and are always constituted of a mixture of structurally related molecules with variation in 1) degree of fatty acid saturation (saturated, mono-unsaturated or di-unsaturated), 2) presence or absence of acetyl groups at C6' and/or C6" atoms, 3) lactonization between the carboxyl end of the fatty acid and either the C4", C6' or C6" atom of the sophorose group resulting in a lactonic sophorolipid or absence of this lactonization, resulting in an open or acidic sophorolipid, 4) fatty acid chain length and 5) (ω) or (ω-1) hydroxylation of the fatty acid (Asmer et al., 1988).

Due to this structural variation, sophorolipids show many interesting applications in a wide range of industrial fields (Banat et al., 2010; Franzetti et al., 2010; Kralova and Sjoblom, 2009; Mulligan, 2009). Since structural composition is reflected in the physico-chemical properties, several industries are particularly interested in specific structural variants. Lactonized sophorolipids have different biological and physicochemical properties compared to acidic forms. In general, lactonic sophorolipids have better surface tension lowering and antimicrobial activity, whereas the acidic ones display a better foam production and solubility (Lang et al., 2000)

On the other hand, acidic sophorolipids have been used as starting molecules for the synthesis of, e.g., dispersible nanoparticles (Kasture et al., 2007) and glycolipid derivatives (Azim et al., 2006; Zerkowski et al., 2006) or have served as source molecules for the production of glucolipids and specialty fatty acids (Rau et al., 2001; Saerens et al., 2009), which are on their turn used for synthesis of polymers (Zerkowski et al., 2007) or precursors for plastics and flavors (Rau et al., 2001). Lactonization reduces the rotational freedom of the molecule; dominance of this type of sophorolipids very often results in the formation of crystals instead of the more common viscous oil, rendering the sophorolipids relatively easy to isolate.

To date, it is impossible to efficiently produce 100% acidic sophorolipids by fermentation with *C. bombicola* ATCC22214.

It is known that the lactonic/acidic balance is to a certain point influenced by fermentation conditions such as the level of yeast extract, oxygen supply and the provided lipidic substrate (Garcia-Ochoa and Casas, 1999). However, it is unclear what mechanism exactly determines the degree of lactonization.

In a typical *C. bombicola* fermentation on glucose and oleic acid, 62% of the sophorolipids are composed of diacetylated lactonic forms, 4% is composed of monoacetylated lactonic forms, and 4% is composed of unacetylated lactonic forms, while the other compounds are constituted of 1',6' lactones and 1',6" lactones (4%), acidic sophorolipids (8%), and other lipids at the end of the cultivation period (Asmer et al., 1988). Hu and Ju (2001b) observed a maximum relative percentage of lactonic forms of 50% using soybean oil and 80% using hexadecane.

In another experiment where palm esters were used, 79.1% occurred in the lactonic form, but when sunflower oil was applied, only 55.6% lactonic sophorolipids were retrieved (Davila et al., 1994). When in a mixed carbon source fed-batch fermentation only oil was added in stationary phase, 13% of the sophorolipids were in the lactonic form (87% acidic); but when a mixture of oil and glucose was fed in stationary phase, 65% were in the lactonic form and, moreover, a much higher production was achieved (Davila et al., 1997). Yeast extract concentration and presence of citric acid influence the ratio of lactonic to acidic sophorolipids too: when yeast extract concentration was 1 g/L, 65% of the sophorolipids occurred in the lactonic form; but when the concentration was increased to 20 g/L, only about 2% were in the acidic form. However, yeast extract concentration is negatively correlated to sophorolipid yield; indeed, with 1 g/L, 76 g/L sophorolipids were obtained at the end of the cultivation period, while this was only 13 g/L for the set-up with 20 g/L (Casas and Garcia-Ochoa, 1999). Addition of 5 g/L of citric acid to the medium increased the percentage of lactonic forms in the sophorolipid mixture of *Candida apicola* (Hommel et al., 1994).

The presence of citrate in the cultivation medium was described to be absolutely necessary to obtain lactonized sophorolipids. It was suggested by Stüwer et al. (1987) that the effects seen for citrate are probably just an effect of the buffering action of the conjugate base of a weak acid. Low pH values lead to the production of acidic sophorolipids (=SLs) and the buffering effect of citrate would thus favor the formation of lactonic SLs. Citrate, on the other hand, is a chelating agent, and metal ions like zinc or calcium could be necessary for the action of a hypothetical enzyme responsible for ring opening. The presence of citrate would in this hypothesis prevent ring opening and, as such, favor the predominance of lactonic SLs in the cultivation medium. Another possibility is that citric acid has some kind of regulatory effect as was described for the regulation of lipid accumulation in oleaginous yeasts (Evans and Ratledge, 1985).

The exact ratio of lactonic to acidic sophorolipids further changes during cultivation with typically more lactonic &

Inns after prolonged incubation times (Casas and Garcia-Ochoa, 1999; Hu and Ju, 2001b).

In brief, one can state that dominance of the acidic forms in the sophorolipid mixture produced by wild-type *C. bombicola* is linked to cultivations under suboptimal conditions and consequently always results in lower yields as compared to the standard conditions described in literature.

Recently, other yeast species producing sophorolipids similar to those of *C. bombicola* were described. In some cases, the lactonic:acidic ratio is different when compared to the ratio for *C. bombicola* obtained under the same cultivation conditions.

In the sophorolipids produced by *C. batistae*, for instance, the acidic forms make up about 60% of mixture compared to 34% for *C. bombicola* (Konishi et al., 2008). The same trend is observed for *C. riodocensis, C. stellata* and *Candida* sp. NRRL Y-27208, which produced predominantly free acid sophorolipids when compared to *C. bombicola* and *C. apicola*. Furthermore, Imura et al. (2010 and JP2008247845) isolated the strain *Candida floricola* TM 1502, which preferentially gives diacetylated acid-form sophorolipids without including lactone-form sophorolipids. The latter strain is the only one described to produce 100% acidic sophorolipids. However, total sophorolipid production is significantly lower when compared to the amounts obtained with *C. bombicola*, hampering the industrial application of this strain.

The only way to obtain acidic sophorolipids in high purity and quantity is via the chemical conversion of natural *C. bombicola* sophorolipid mixtures to acidic products by alkaline hydrolysis. By this conversion, however, all other ester-bonds will be hydrolyzed as well, resulting in the removal of any present acetyl groups and the consequent production of only acidic unacetylated sophorolipids.

Until now, it remained unclear how and when lactonization occurred. On the one hand, spontaneous lactonization of aqueous solutions of acidic non-acetylated sophorolipids has been observed, suggesting a spontaneous process. Furthermore, the presence of citrate is claimed to influence the lactonic:acidic ratio (Hommel et al., 1994; Stüwer et al., 1987). On the other hand, Hommel et al. (1994) suggest the involvement of a cell wall-bound lipase in the lactone formation. In this regard, it was demonstrated that the commercial Novozyme 435 or lipase B from *Pseudozyma antarctica* (former *C. antarctica*) can, under rather non-physiological laboratory conditions, lactonize an acidic unacetylated sophorolipid ester at the 6"-position in anhydrous tetrahydrofuran (Bisht et al., 1999; Nunez et al., 2003).

Furthermore, Van Bogaert et al. (2011) recently reviewed the microbial synthesis of sophorolipids. In this review, the authors indicate that it is believed that a specific lactone esterase mediates lactonization of sophorolipids in *C. bombicola* but that no such enzyme has been identified.

Taken together, it is clear that identification of an alternative enzyme responsible for an efficient lactonization would offer great potential in the control of structural variability in the sophorolipid production and production of a specific sophorolipid mixture.

However, there was until now not a single hint in the art indicating if and where such an enzyme could be found in the genome of *C. bombicola*, and/or what the role of citrate is, and/or if multiple enzymes or a single enzyme are/is fully responsible for the lactonization process.

DISCLOSURE

The disclosure relates to the identification of a single enzyme responsible for an efficient lactonization offering great potential in the control of structural variability in the sophorolipid production and production of a specific, less heterogeneous sophorolipid mixture without the need of additional chemical treatments.

In order to try to identify an alternative enzyme responsible for an efficient lactonization, the annotated genome of *C. bombicola* was screened in the presence of putative lipases. Twenty-five (25) predicted proteins displayed putative lipase domains and nine of them were annotated as putative lipases sensu stricto. One of the nine putative lipases was evaluated as a lipase belonging to Class 3, which is composed of enzymes that are not closely related to other lipases and, therefore, might possess other (secondary) activities. However, knocking out this gene in *C. bombicola* did not result in the partial or complete loss of the lactonizing abilities of the mutant and the mutant did not lose its ability to hydrolyze rapeseed oil triglycerides as well.

Another putative esterase was evaluated based on input from comparative proteomics experiments. When extracellular protein fractions obtained from sophorolipid producing *C. bombicola* cells were analyzed, a putative lipase was unexpectedly found among the most abundant proteins. Surprisingly, a single knock-out of this lactonase gene resulted in complete absence of any lactonic form in any sample and any tested condition, despite the potential presence of the other putative, functional lipase genes that might be involved in lactonization. Moreover, the total sophorolipid yields for the wild-type and the mutant were comparable, which is surprising in view of previous manipulations of the sophorolipid biosynthetic pathway. Indeed, a simple knock-out of the acetyltransferase gene, leading to the production of non-acetylated sophorolipids, resulted in a production of only 5 g/L of sophorolipids, even when rapeseed oil was added (Saerens et al., 2011b). Furthermore, when aiming for the production of glucolipids by disabling the second glucosyltransferase of the sophorolipid biosynthetic pathway, again a strong decrease of biosurfactant production was observed (Saerens et al., 2011a).

Remarkably, although disabling a translated and highly expressed putative lipase gene, rapeseed oil can still serve as a carbon source or hydrophobic substrate for sophorolipid production in the lactonase negative strain.

The disclosure thus relates to the identification of a lactonase gene from *Candida (Starmerella) bombicola* which is, on its own, fully responsible for the lactonization of sophorolipids. Indeed, deletion of the gene surprisingly results in a yeast species producing only acidic sophorolipids (see FIG. 1). With this new structural composition, the created mutant offers a one-step production technology for the fermentative synthesis of industrially important molecules making use of cheap, renewable substrates. Up to date, it was not possible to produce a sophorolipid mixture with this structural composition with *C. bombicola*. Due to the higher foaming capacity and better water solubility of the mutant mixture, these compounds have unique properties and show better performances for several applications such as use as detergent, in pharmaceutical applications, in cosmetic applications, etc.

The disclosure thus relates to a polypeptide comprising an amino acid sequence given by SEQ ID NO:2 having lactonase activity, or a fragment thereof retaining the lactonase activity or a variant thereof having at least 34% sequence identity with SEQ ID NO:2 and having the lactonase activity. It is further clear that the polypeptide comprising an amino acid sequence given by SEQ ID NO:2 or a fragment or a variant thereof is/are fully responsible for the lactonization of sophorolipids in *C. bombicola*. More specifically, the disclosure relates to a variant as indicated above comprising an amino acid sequence given by SEQ ID NO:33. The latter amino acid sequence corresponds to the lactonase of *C. bombicola* of the disclosure, which is produced in *Pichia pastoris* via recombinant methods (see also Example 4). Moreover, the disclosure relates to a fragment or a variant as indicated above wherein the fragment or variant comprises the amino acid serine on the amino acid position corresponding to position 181 of SEQ ID NO:33. Indeed, the disclosure describes in Example 6 (see further) that the amino acid serine (=S or Ser), which is part of the conservative motif GYSGGA (=SEQ ID NO:44) and which is present at position 181 of the lactonase corresponding to SEQ ID NO:33 of the disclosure, is important for the lactonase activity. Hence, the amino acid is an important amino acid that is preferably present in the polypeptides, fragments and/or variants of the disclosure.

The disclosure further relates to a nucleic acid encoding for a polypeptide, fragment or variant as indicated above and, more specifically, to a nucleic acid as indicated above wherein the nucleic acid consists of the nucleic acid sequence given by SEQ ID NO:1 or SEQ ID NO:32. SEQ ID NO:32 is disclosed in detail in Example 4. The disclosure further relates to any vector comprising a nucleic acid as indicated above and any host cell comprising the latter vector. Some non-limiting examples of specific vectors and host cells are described further in the present "Description" and/or in the "Examples" section.

The nucleic acid sequence as depicted by SEQ ID NO:1 corresponds to the following open reading frame of 1233 base pairs and the protein sequence of the enzyme of the disclosure is depicted by the following 410 amino acid sequence SEQ ID NO:2:

```
SEQ ID NO: 1:
ATGCTGGCTCTGTTTTTTTCGCTTGCGCCTCTACTTTCTCAAGCTCTCCC

TTTAGGCTATACTGCGGCCCCCGCTGAATCATTCTATTTTTGGCCAGAGA

ACATATCCAGCCTCCAAGCTGGCGAGATTTTTAGAAAACGGGAACTCTTA

ACTCTCCCAGACATCTTTGACTTTGGCCCTAATCTGGAAAAGGTCGTACA

AGTGGCTTACAAAACCGTCTCACCGATGGCAATGACTCGTTTTCCATCG

CCAGTATCTTTATCCCTAAGAATCCAAGCCCAGAACTCAAACTTTACTCT

TATCAGACGTTTGAGGATGCCGTGCAGCTTGATTGTGCCCCAAGCTATGC

TTTAGAAGTGGGTAACAAGTCCAGCAACTATCTTCCTGTCACTAGCAATT

TATCTGCCATCAGTCGAGAACTTGAGAAAGGACGTCACTGCATTATCCCT

GATCACGAGGGCTATATTTCAGGATTCTTTGCAGGACGGCAGGAGGGATA

TGCTGGTTTAGACGGAATTCGCGCTGCTCGAAACTATCTCAATGGCACCA

ACGAGACCCCAATTGGTATCTTCGGATACAGTGGAGGTGCACAAGCAACG

GCCTGGATTGTTGATTTGCATGACGAGTATGCTCCTGACTTGAACTTTGT

TGGAACAGTTTCTGGAGGCACTTTGGTTGACGCTTGGGGCACTTTTCAGT

ATATCGACTATCCGAAGGTGTATCTAAAGGGCAGCATTCTTATCATGTAT

ACGGGTCTTTTTTCAGGTTATCCAGCTCAATTTGAGGTGATTTGGCCATA

TATTGAGCCTGTAATTCAAGAAAACATGCTACTGCTACGTTTGGCGCCGA

ATGATTGTAACCAAAGCCCGATACTTCAAGGTTACAACAATTCAATCATG

GCCGGTATACATGTGGACCTTCCCGAATTCCCTGCTTCTAAGTACATATT

CCAGCACGAGTCCCTCCTTGCCAACTACAGCGTAGTGCCAGTTTCCACAC

CGAAGTTTCCTCGCTACATGTACCATGGTGGATCTGATGAGTTGGCCAAA

TTGAGCCTTGTCGAGCAGTATGTTGATCAACAATGGAATACCGGCGCTAA

TCTCACCTTCGTGGTGTATCCGGGTCTTCTTCATGACGAGACGGCTTACC

GTGGCTTTGATGCCGCGATGGATTGGCTTGATGCCCAGCTCGATAGTGGA

TACCTTCCACCTGTAAACTCAACTCATACATGA

SEQ ID NO: 2:
MLALFFSLAPLLSQALPLGYTAAPAESFYFWPENISSLQAGEIFRKRELL

TLPDIFDFGPNLEKVVQVAYKTRLTDGNDSFSIASIFIPKNPSPELKLYS

YQTFEDAVQLDCAPSYALEVGNKSSNYLPVTSNLSAISRELEKGRHCIIP

DHEGYISGFFAGRQEGYAGLDGIRAARNYLNGTNETPIGIFGYSGGAQAT

AWIVDLHDEYAPDLNFVGTVSGGTLVDAWGTFQYIDYPKVYLKGSILIMY

TGLFSGYPAQFEVIWPYIEPVIQENMLLLRLAPNDCNQSPILQGYNNSIM

AGIHVDLPEFPASKYIFQHESLLANYSVVPVSTPKFPRYMYHGGSDELAK

LSLVEQYVDQQWNTGANLTFVVYPGLLHDETAYRGFDAAMDWLDAQLDSG

YLPPVNSTHT
```

The terms "nucleic acid" and a "fragment" or a "variant" thereof corresponds, for example, to DNA, cDNA, RNA, sense and anti-sense nucleic acids and the like.

The term "fragment" specifically refers to a nucleic acid sequence containing fewer nucleotides than the nucleic acid sequence as depicted by SEQ ID NO:1 or SEQ ID NO:32 and that encodes for a protein retaining the lactonase activity. The teem "variant" specifically refers to a nucleic acid encoding for a protein having at least 34% sequence identity, preferably having at least 51 to 70% sequence identity, more preferably having at least 71 to 90% sequence identity or, most preferably, having at least 91, 92, 93, 94, 95, 96, 97, 98 or 99% sequence identity with SEQ ID NO:2 or SEQ ID NO:32 or with a fragment thereof, and, that encodes for a protein retaining the lactonase activity.

The term "fragment" further refers to a protein (or peptide or polypeptide) containing fewer amino acids than the amino acid sequence as depicted by SEQ ID NO:2 and that retains the lactonase activity. Such fragment can, for example, be a protein with a deletion of 10% or less of the total number of amino acids at the C- and/or N-terminus. Some specific fragments of the disclosure comprise the amino acid serine on the amino acid position corresponding to position 181 of SEQ ID NO:33 as indicated above. The term "variant" refers to a protein having at least 34% sequence identity, preferably having at least 51 to 70% sequence identity, more preferably having at least 71 to 90% sequence identity or, most preferably, having at least 91, 92, 93, 94, 95, 96, 97, 98 or 99% sequence identity with SEQ ID NO:2 or with a fragment thereof, and that encodes for a protein retaining the lactonase activity. A specific variant of the disclosure is the polypeptide comprising an amino acid sequence given by SEQ ID NO:33 as indicated above.

Hence, orthologues, or genes in other genera and species (than the strain *Candida bombicola* ATCC 22214 from which SEQ ID NOS:1 and 2 are derived) that encode for a polypeptide with at least 34% identity at amino acid level, and having the described function are part of the disclosure. The percentage of amino acid sequence identity is determined by alignment of the two sequences and identification of the number of positions with identical amino acids divided by the number of amino acids in the shorter of the sequences×100. The latter variant may also differ from the protein as depicted by SEQ ID NO:2, only in conservative substitutions and/or modifications, such that the ability of the protein to have lactonase activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be proteins as described herein modified by, for example, the deletion or addition of amino acids that have minimal influence on the lactonase activity as defined above, secondary structure and hydropathic nature of the enzyme. Furthermore, the teen "variants" also refers to any glycosylated protein or fragments thereof as described above.

In addition, the identification of the lactonase gene as the single gene responsible for lactonization of sophorolipids, enables the creation of an overexpression mutant where lactonized sophorolipids are remarkably enriched, with the mutant mixture thus being deprived of acidic sophorolipids. Because of the significantly better surface tension lowering and antimicrobial activity, such mutant mixture attracts the attention of the pharmaceutical and medical industries. Hence, the disclosure relates to the usage of a polypeptide, a fragment and/or a variant as defined above to lactonize or to polymerize carbohydrate-containing compounds, lipids, fatty acids, hydroxylated fatty acids, alcohols, dicarboxylic acids or mixtures thereof and, more specifically, to the usage as defined above wherein the carbohydrate-containing compounds are preferably sophorolipids. The disclosure further relates to methods to lactonize or to polymerize carbohydrate-containing compounds, lipids, fatty acids, hydroxylated fatty acids, alcohols, dicarboxylic acids or mixtures thereof comprising: a) providing an isolated polypeptide, fragment or variant as defined above, and b) contacting the carbohydrate-containing compounds, lipids, fatty acids, hydroxylated fatty acids, alcohols, dicarboxylic acids or mixtures thereof with the isolated polypeptide, fragment or variant as defined above. The latter carbohydrate-containing compounds are preferably sophorolipids. Some specific, but non-limiting embodiments of the latter methods or assays are described further in the Examples section (e.g., Example 3 relating to the usage of a lactonase overexpressing yeast and Example 5 relating to activity assays with the lactonase).

The disclosure thus also relates to a modified host cell that is transformed with an exogenous nucleic acid as defined above or that over-expresses an endogenous nucleic acid as defined above.

In other words, the disclosure relates to the usage of the proteins/polypeptides/peptides/fragments/variants having lactonase activity as described above to lactonize carbohydrate-containing compounds (such as sophorolipids, cellobioselipids, or alkylglucosides), or lipids, fatty acids, or hydroxylated fatty acids. In other words, to form intra-molecular ester-bounds.

Furthermore, the disclosure relates to the usage of the proteins with a (partial) sequence identical or similar to SEQ ID NO:2 or SEQ ID NO:33 for the polymerization of acidic sophorolipids, glycolipids, fatty acids, hydroxylated fatty acids, dicarboxylic acids or mixtures thereof. In other words, the disclosure relates to the formation of inter-molecular ester-bounds.

The term "lactonase activity" thus relates to the formation of intra-molecular or inter-molecular ester-bounds as indicated above.

Hence, the disclosure relates to the usage of a modified host strain expressing a protein having lactonase activity as described above to lactonize or polymerize carbohydrate-containing compounds (such as sophorolipids, cellobioselipids, or alkylglucosides), or lipids, fatty acids, hydroxylated fatty acids, alcohols, dicarboxylic acids or mixtures thereof. In this regard, the disclosure relates to the usage as described above wherein the modified host strain is transformed with an exogenous nucleic acid sequence as described above or wherein the modified host strain over-expresses an endogenous nucleic acid sequence as described above. As such, the disclosure relates to the usage as described above, wherein the modified host strain is a bacterium, a fungus, a yeast, an insect cell, a plant cell or an animal cell.

The disclosure further relates to the usage of a modified host cell as described above to produce sophorolipids or, more specifically, to produce at least 90% lactonic sophorolipids of the total sophorolipid production. Indeed, the disclosure describes (see, e.g., Example 3) that usage of an overexpression mutant of this disclosure is capable of resulting in a commercially important increase of the total yield of sophorolipids. The disclosure described herein further discloses (see also, e.g., Example 3) that the sophorolipids produced by the overexpression mutants were strongly enriched in the lactonic forms. With the teen "strongly enriched" is meant more than 50%, 60% or 70%, preferably more than 75%, 80% or 85%, and most preferably more than 90%, 95% or 99% of lactonic forms versus the total amount of sophorolipids.

The disclosure further relates to the usage of a modified host cell as described above to produce at least 50% lactonic sophorolipids in a medium lacking citrate. A specific, non-limiting embodiment of the latter aspect of the disclosure is described further in Example 3 (result 3.2.1).

The disclosure further relates to a modified host cell comprising a nucleic acid as defined above that has lost its capability to encode for a polypeptide, fragment or variant as defined above, or, wherein the polypeptide, fragment or variant as defined above has lost its lactonase activity. The disclosure further relates to the usage of a modified host cell as defined above to produce acidic sophorolipids. The disclosure further specifically relates, as is also described further, to the usage of a modified host cell as defined above to produce at least 50%, 60%, 70%, 80%, 90%, or, most preferably, 100% of acidic sophorolipids compared to the total amount of sophorolipids that are produced by the host cell.

The term "host cell" relates to any possible host cell but specifically relates to a "fungal species capable of producing sophorolipids" referring to a phylogenetically diverse group of yeasts (predominantly Ascomycetes and few Basidiomycetes), which spontaneously synthesize sophorolipids constituted of the sugar sophorose attached to a hydroxylated fatty acid (see FIG. 2). The phylogenetically diverse group of yeasts comprises the species *Candida apicola* (Gorin et al., 1961), which was initially identified as *Torulopsis magnolia*, *C. bombicola* (Spencer et al., 1970; recently referred to as *Starmerella bombicola*), *Wickerhamiella domericqiae* (Chen et al., 2006), *Rhodotorula bogoriensis* (Tulloch et al., 1968; initially called *Candida bogoriensis*), *Candida batistae* (Konishi et al., 2008), *Candida floricola* (Imura et al., 2010), *Candida riodocensis, Candida stellata* and *Candida* sp. NRRL Y-27208 (Kurzman et al., 2010) and other species of the so-called *Starmerella* clade, which incorporates over 40 species. More specifically, the disclosure relates to host cells as described above, wherein *Candida (Starmerella) bombicola* is the strain *Candida (Starmerella) bombicola* ATCC 22214 (CBS 6009).

The term "modified" specifically refers to a modified yeast species or yeast strain characterized in having at least one mutation in a nucleic acid molecule of the disclosure encoding for a lactonase of the disclosure. The term "mutation" refers to a spontaneous mutation and/or to an induced mutation in the genome of the yeast strain. The mutation can be a point mutation, deletion, insertion or any other type of mutation. "Mutation" most specifically refers to knock outs (KO) via insertion of a KO cassette. Inducing a mutation in the genome of a yeast strain can be undertaken by any method in the art known by a skilled person, such as the insertion of a KO cassette into a gene of interest. Similarly, tracing or detecting whether there is a mutation in the genome of a modified strain, compared to a wild-type strain, can also be determined by any method known in the art.

The term "sophorolipids" (see FIG. 2) refers to carbohydrate-based, amphiphilic biosurfactants that are constituted of the sugar sophorose attached to a hydroxylated fatty acid/ alkyl chain, i.e., hydroxylated fatty acid/alkyl chains, wherein the fatty acid/alkyl chain contains 5 to 26 carbon atoms. Preferably, and especially with regard to *C. bombicola*, the fatty acid chain is composed of 16 or 18 C-atoms. More specifically, sophorolipids refers to glycolipid biosurfactants that are constituted of a sophorose head group(2-O-β-D-glucopyranosyl-β-D-glucopyranose) from which the anomeric C-atom is attached to an (ω) or (ω–1) hydroxylated $C_{10}$, $C_{12}$, $C_{14}$, $C_{16}$, $C_{18}$, $C_{22}$ or $C_{24}$ fatty acid. They occur either as open-ring structures (acidic form) or as lactones (closed-ring structures or lactonic form or lactonized form) with an intra-esterification between the fatty acid carboxyl group and the 4", 6' or 6" carbon atom of the sophorose head group. In addition, acetyl groups can be attached at the 6' and/or 6" positions (Asmer et al., 1988).

The term "acid sophorolipids" refers to sophorolipids without a free fatty acid carboxylic ending, so the fatty acid carboxylic ending is not being intra-molecularly esterified at the C4", C6", C6' or any other atom.

The term "the production of acidic sophorolipids" refers to the production of a mixture that is less complex (as shown in FIG. 1) as compared to the mixture that one obtains in a typical wild-type *Candida bombicola* fermentation (Asmer et al., 1988). Indeed, the mixture of the disclosure is preferably deprived from lactonic forms. In other words, no lactonic forms can be detected, using well-known methods, in the mixture of the disclosure.

Hence, the mixture of the disclosure comprises at least 50%, i.e., 50, 55, 60, 65, 70, 75, 80, 85, 90, 95, 96, 97, 98, 99 or 100% of acidic sophorolipids.

The disclosure thus relates to a modified fungal strain belonging to a fungal species capable of producing sophorolipids as described above, characterized in that the fungal strain, compared to an unmodified wild-type strain: a) has at least one mutation in the gene encoding for the lactonase of the disclosure, and b) produces a mixture comprising at least 50% entirely acidic sophorolipids, preferably 100% entirely acidic sophorolipids.

The disclosure relates to the usages as described above, wherein the mutation is a deletion in the lactonase of the disclosure.

The disclosure thus relates to the usage of a nucleic acid molecule as defined above, having lost its capability to encode for a functional lactonase or to the usage of a polypeptide as defined above, having lost its lactonase activity to produce a mixture comprising entirely unacetylated sophorolipids. A nucleic acid molecule having lost its capability to encode for a functional lactonase as defined above can be obtained by mutation or by any known means to silence the transcription or translation of the nucleic acid, such as the insertion of a nucleic acid fragment, a marker gene or others in the functional coding or non-coding part of the lactonase gene, a mutation or removal of the functional coding or non-coding part of the lactonase gene, the usage of specific siRNAs, miRNAs, combinations thereof, or any other way. Similarly, a polypeptide as defined above, having lost its lactonase activity, can be obtained by any (small) compound or other means to disrupt the function of the lactonase of the disclosure. Means to silence the transcription or translation or means to disrupt the function of the lactonase of the disclosure or means to disrupt the function of a necessary regulator/ activator protein of the lactonase thus comprise the usage of any molecule such as, but not limited to, an antibody, an amino acid, a peptide, a small molecule, an aptamer, a ribozyme, an oligoribonucleotide sequence such as dsRNA used to initiate RNA interference (RNAi) or an anti-sense nucleic acid. Such a molecule is thus capable of binding with a lactonase protein or an activator/regulator protein thereof or is capable of interfering with the cellular synthesis of lactonase or of an activator/regulator thereof by, for example, binding and degrading mRNA's encoding for a lactonase protein or an activator/regulator thereof.

The disclosure and the above-indicated usages will be illustrated by the following non-limiting examples.

BRIEF DESCRIPTION OF THE FIGURES

FIG. 1: The major, but not the sole, components of the new sophorolipid mixture produced by the lactonase-negative strain. R=H or $COCH_3$ (Panel a) acidic 17-O-sophorosyl-octadecanoic acid; (Panel b) acidic 17-O-sophorosyl-octadecenoic acid.

DETAILED DESCRIPTION

Examples

Example 1

Figure 2:
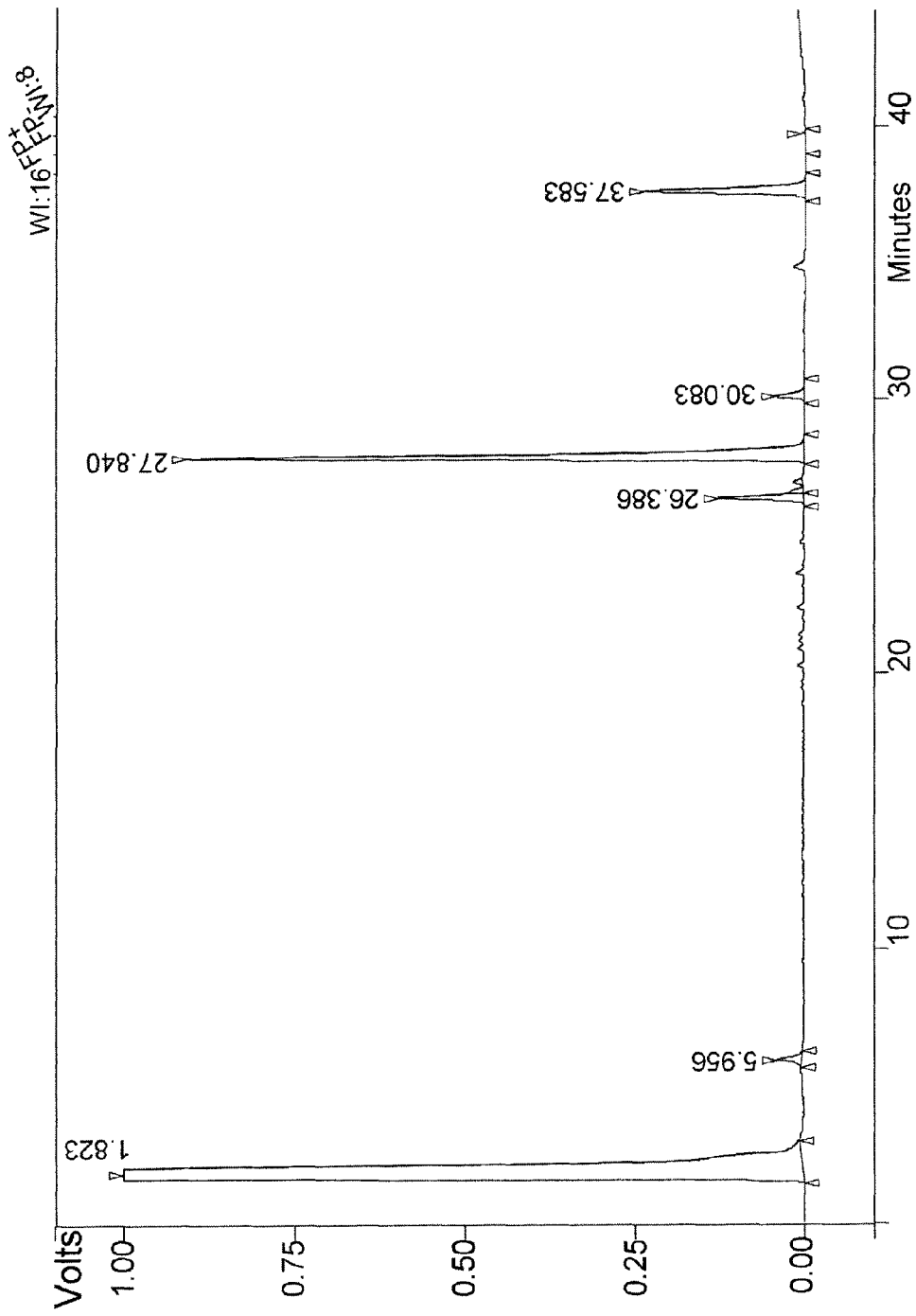
FIGS. 2A and 2B: Sophorolipids typically produced during fermentation are considered to be a mixture of compounds represented by formulas (FIG. 2A) acidic form and (FIG. 2B) lactonic form.

Occurrence of a Putative Lipase Gene in the Secretome of Sophorolipid-Producing *C. bombicola* Cells 1.1 Material and Methods
1.1.1 Secretome Preparation

*C. bombicola* ATCC 22214 was cultured for eight days in 150 ml Lang medium (Lang et al., 2000). The cells were separated from the medium by centrifugation at 4,000 rpm for 15 minutes (4° C.). The medium liquid was subsequently filtered twice on a 0.22 μm filter to exclude any cellular trace. A protease inhibitor cocktail (complete, EDTA-free Protease Inhibitor Cocktail Tablets, Roche) was added to prevent protein degradation. Consequently, the protein fraction in the collected medium was enriched and concentrated to a volume of 30 ml using a Stirred Ultrafiltration Cell (Model 8200) with a 10 kDa molecular weight cut-off membrane (Sartorius-Stedim 14439-63-D). Next, proteins were further concentrated by ultrafiltration in VIVASPIN® 15R columns (MWCO 10 kDa, Vivaproducts) to a volume of 5 ml. The centrifugation was performed at 4,000 rpm at 4° C. and the sample was mixed every 15 minutes to avoid precipitation.

1.1.2 SDS-PAGE

Five μl of the sample was mixed with 20 μl of Laemmli buffer, boiled for 5 minutes and loaded on a 12.5% SDS-PAGE gel. The gel was stained with Coomassie Brilliant Blue G250 overnight and later destained in 30% MeOH.

1.1.3 Tryptic Digestion

The total SDS-PAGE gel lane was divided into 17 fractions. The gel pieces were destained by 3×20-minute incubation cycles at 30° C. with 150 μl of a 50% acetonitrile (ACN)/200 mM $(NH_4)_2CO_3$ mixture. The proteins were digested in gel (according to Shevchenko et al., 2007) by adding 8 μl of 0.002 μg/μl trypsin (Promega) in 50 mM $(NH_4)_2CO_3$ during overnight incubation in 37° C. The peptides were collected from the supernatant. The gel pieces were further extracted with 60 μl of 60% ACN/0.1% FA during a 20-minute incubation at 30° C. After that, samples were vortexed for 3 minutes, shortly centrifuged and extraction was repeated with 20 μl of 60% ACN/0.1% FA. These extracts were pooled with the supernatant and the resulting peptide mixture was dried using vacuum centrifugation and dissolved in 15 μl of 2% ACN/0.1% FA.

1.1.4 NanoLC-ESI-FT MS Analysis

Five μl of the extracted peptides were loaded on a ZORBAX® 300SB-C18 analytical column 150 mm×75 μm (Agilent) connected to an Agilent 1200 chromatographic system (Agilent, Santa Clara, Calif., USA) coupled to an LTQ-FTUltra mass spectrometer (Thermo Fisher Scientific, Waltham, Mass.), as described in de Graaf et al. (2010). The separation was performed by reversed phase chromatography using a 50-minute linear gradient ranging from 2% buffer A to 80% buffer B at a 300 nl/minute flow rate. The mobile phase buffer A was 99.9% water with 0.1% formic acid. Mobile phase B was 99.9% acetonitrile with 0.1% formic acid. The LC eluent was directly coupled to a TRIVERSA NANOMATE® ESI source (Advion, Ithaca, N.Y.), working in the nanoLC mode and being equipped with D-chips upon which a 1.55-kV voltage was applied.

The FT-ICR mass analyzer acquired MS scans at 100,000 resolution during the LC separation. The three most intense precursor peptides for each MS scan were automatically selected and fragmented by the LTQ ion trap mass analyzer.

1.1.5 Database Search

Raw LC-MS/MS data received from the FT-ICR MS measurements were analyzed using Mascot Daemon version 2.3.2. To identify proteins, Mascot version 2.3.01 searches were performed against the in-house available primary annotated *C. bombicola* genome containing 4617 genes, predicted from three contigs using the Augustus algorithm, together with its decoy database created on the flight by Mascot software. The MS/MS data from the 17 SDS-PAGE bands were merged into one single search file. The following search settings were applied: data were imported with the Thermo Finnigan LCQ/DECA RAW filter, maximum two missed cleavages of trypsin were allowed, and an oxidation (M) was set up as variable modification. As instrument parameters, the ESI-FTICR instrument was selected with a possible MS/MS error tolerance of 0.5 Da and peptides error tolerance of 10 ppm. All peptides with a significance threshold higher than 0.01 and an ion score cutoff lower than 30 were discarded. We accepted proteins with two or more peptide hits within the above criteria.

The protein abundance, expressed as an EmPAI value (Rappsilber et al., 2002), was calculated by Mascot using the number of observable peptides $N_{obsd}$ and the number of the observed peptides $N_{obsbl}$ for a parent ion:

$$emPAI = 10^{PAI} - 1 \text{ where } PAI = N_{obsd}/N_{obsbl}$$

Protein contents in molar and weight fraction percentages are described as:

Protein content (mol %)=(emPAI/ΣemPAI)×100

Protein content (weight %)=(emPAI×$M_r$)/Σ(emPAI× $M_r$))×100

Where $M_r$ is the molecular weight of the protein, and ΣemPAI is the summation of the emPAI values for all identified proteins.

1.2 Results

Figure 3:
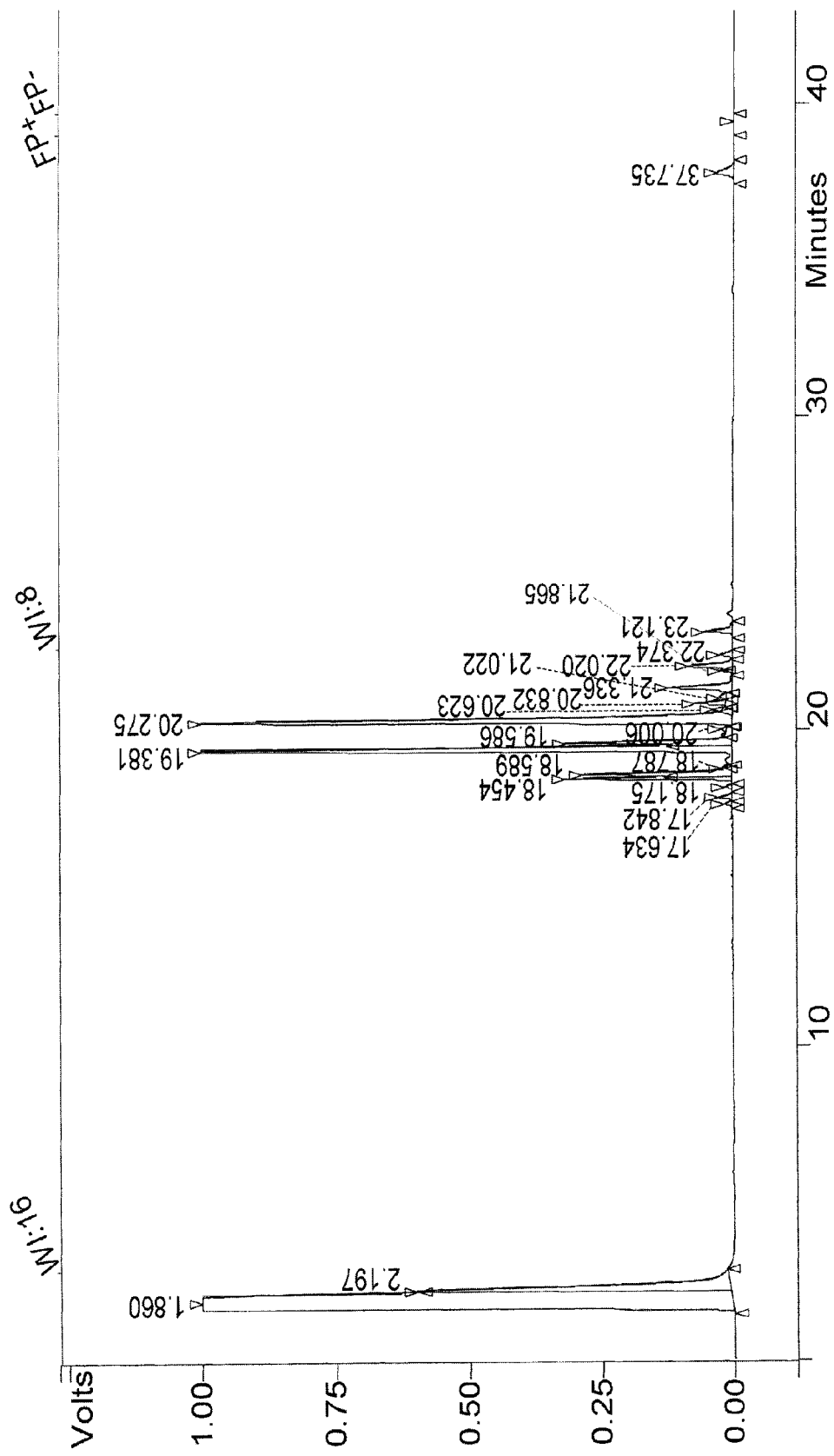
FIG. 3: The identified peptides of a putative lipase are marked in bold. The peptides cover 14% of the sequence.
Figure 4:
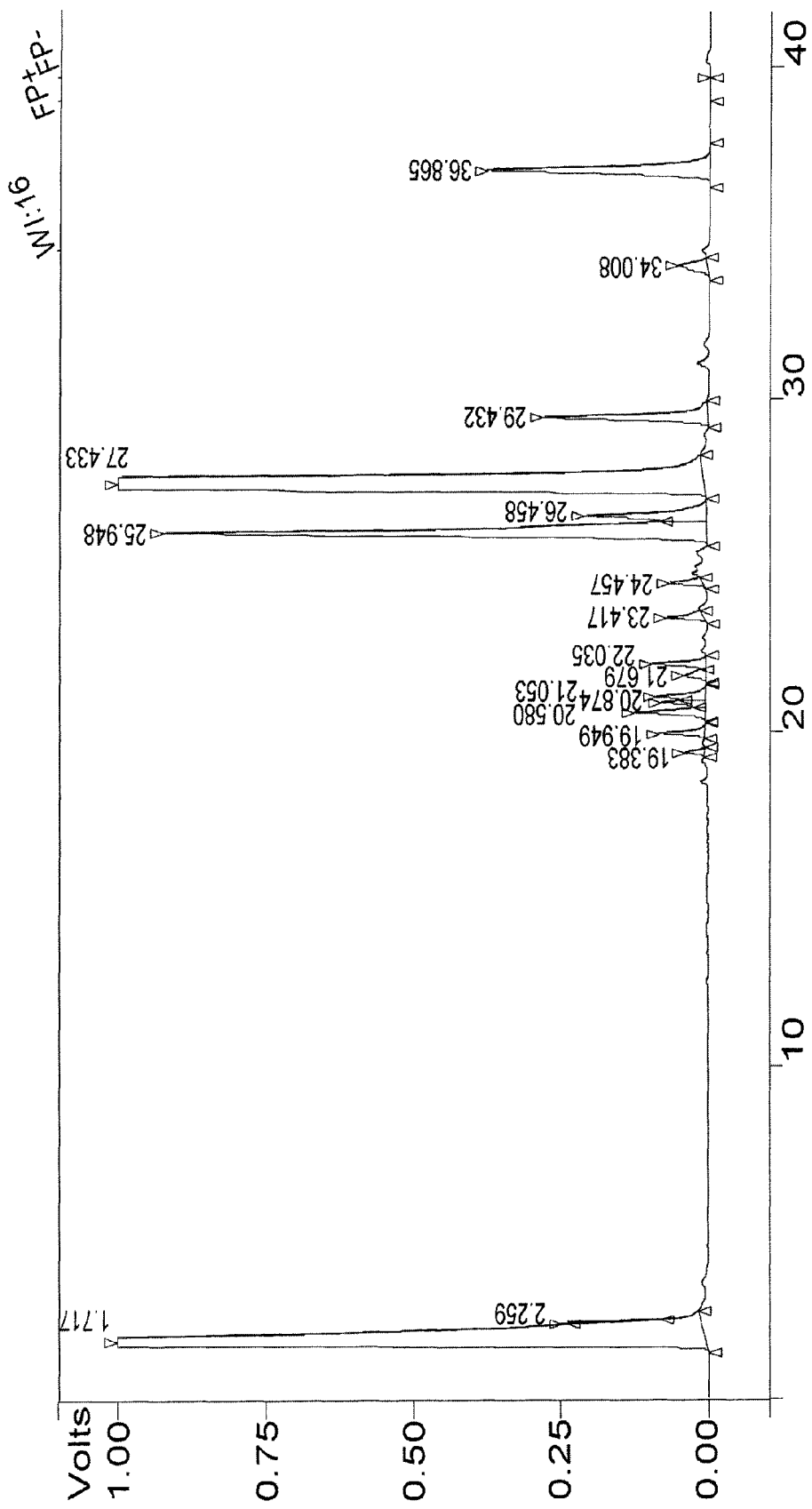
FIGS. 4A and 4B: HLPC-ELSD chromatogram of sophorolipids produced by the wild-type (FIG. 4A (upper part)) and lactonase knock-out strain (FIG. 4B (lower part)) without the addition of rapeseed oil. Lactonic sophorolipids elute between 25 and 31 minutes, acid ones between 17 and 24 minutes. LC-MS analysis identified the peaks at 19.4 and 20.3 minutes as non-acetylated acid sophorolipids with a C18:1 and C18:0 fatty acid chain, respectively. The peaks between 20.4 and 23.6 originated from mono- and di-acetylated acidic sophorolipids. The peak at 28.8 is generated by di-acetylated lactonic C18:1 sophorolipids.
Figure 5:
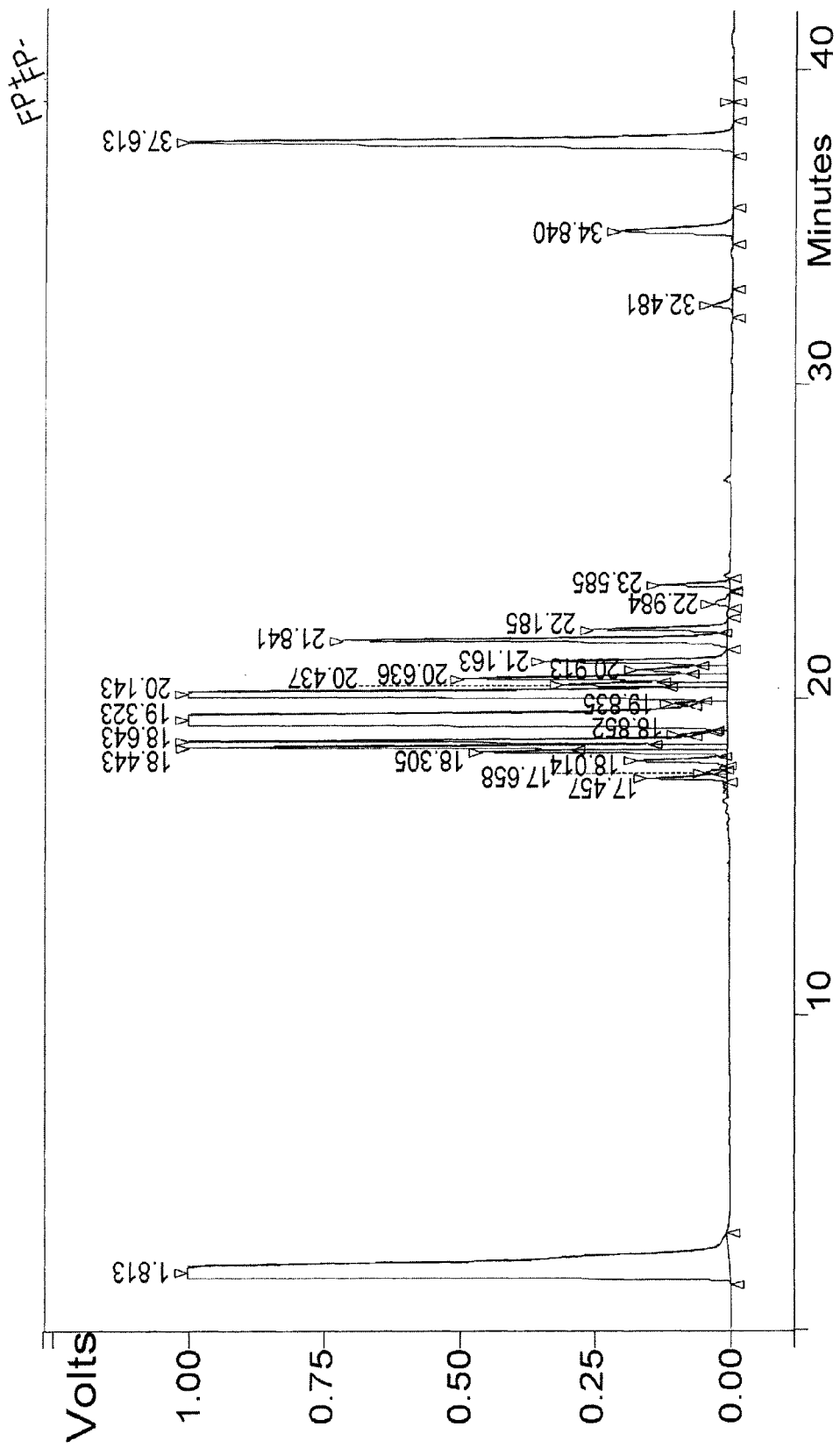
FIGS. 5A and 5B: HLPC-ELSD chromatogram of sophorolipids produced by the wild-type (FIG. 5A (upper)) and lactonase knock-out strain (FIG. 5B (lower)) with addition of rapeseed oil. Lactonic sophorolipids elute between 25 and 31 minutes, acid ones between 17 and 24 minutes. Free fatty acids derived from rapeseed oil elute between 30 and 40 minutes. LC-MS analysis identified the peaks at 19.3 and 20.1 minutes as non-acetylated acid sophorolipids with a C18:1 and C18:0 fatty acid chain, respectively. The peaks between 20.4 and 23.6 originated from mono- and di-acetylated acidic sophorolipids. The peak at 27.4 is generated by diacetylated lactonic C18:1 sophorolipids.

In the secreted protein fraction (secretome) from *C. bombicola* obtained after eight days of growth, 31 proteins were identified. Between them, a putative lipase was found with a protein score of 14222 (score cut off=30) and seven unique peptides. In FIG. 3, these peptides are marked. In Table 1, detailed information about those peptides can be found, including Mascot scores that indicate the quality of the identification.

TABLE 1

Detected lactonase peptides and their expected value and ion score calculated by Mascot version 2.3.01

| Nr. | Score | Expect | Peptides |
|---|---|---|---|
| 1 | 51 | 8.6e-006 | K.NPSPELK.L (SEQ ID NO: 21) |
| 2 | 56 | 3.3e-006 | K.VVQVAYK.T (SEQ ID NO: 22) |
| 3 | 91 | 1.3e-009 | R.QEGYAGLDGIR.A (SEQ ID NO: 23) |
| 4 | 70 | 1e-007 | R.YMYHGGSDELAK.L (SEQ ID NO: 24) |
| 5 | 36 | 0.00026 | R.YMYHGGSDELAK.L (SEQ ID NO: 24) |
| 6 | 39 | 0.00014 | R.YMYHGGSDELAK.L + Oxidation (M) (SEQ ID NO: 25) |
| 7 | 67 | 1.9e-007 | R.YMYHGGSDELAK.L + Oxidation (M) (SEQ ID NO: 25) |
| 8 | 94 | 7.4e-010 | R.ELLTLPDIFDFGPNLEK.V (SEQ ID NO: 26) |
| 9 | 62 | 1.2e-006 | R.ELLTLPDIFDFGPNLEK.V (SEQ ID NO: 27) |
| 10 | 80 | 2.3e-008 | K.RELLTLPDIFDFGPNLEK.V (SEQ ID NO: 28) |
| 11 | 73 | 9.4e-008 | R.KRELLTLPDIFDFGPNLEK.V (SEQ ID NO: 29) |
| 12 | 43 | 6.8e-005 | R.KRELLTLPDIFDFGPNLEK.V (SEQ ID NO: 29) |

The Mascot software automatically calculates the anemPAI factor for each protein. For the lipase, the calculated emPAI factor is 1.39, which corresponds to 3.72 mol % and 3.17 weight %, respectively, of the protein content of the eight-day-old secretome.

Example 2

Creation of a Lactonase-Negative *C. bombicola* Strain for the Production of Acidic Sophorolipids 2.1 Material and Methods 2.1.1 Strains and Culture Conditions

*Candida bombicola* ATCC 22214 was used as the parental or wild-type strain. *Candida bombicola* PT36, an ura3 autotrophic mutant, was derived from this parental strain and used to construct both the knock-out and overexpression strains. When sophorolipid production was intended, the medium described by Lang et al. (2000) was used. 37.5 g/L rapeseed oil was added two days after inoculation. Yeast cultures were incubated at 30° C. and 200 rpm for a total time of ten days.

*Escherichia coli* DH5α cells were used in all cloning experiments and were grown in Luria-Bertani (LB) medium 1% trypton, 0.5% yeast extract and 0.5% sodium chloride) supplemented with 100 mg/L ampicillin. Liquid *E. coli* cultures were incubated at 37° C. and 200 rpm.

2.1.2 DNA Isolation and Sequencing

Bacterial plasmid DNA was isolated with the QIAPREP® Spin MINIPREP™ Kit (QIAGEN®). All DNA sequences were determined at LGC Genomics (Berlin, Germany).

2.1.3 Transformation

*C. bombicola* cells were transformed by electroporation. Transformants were selected on synthetic dextrose (SD) plates (0.67% yeast nitrogen base without amino acids (DIFCO) and 2% glucose). *E. coli* cells were transformed as described by Inoue et al. (1990).

2.1.4 Creation of the Knock-Out Cassette

A total fragment of 1944 bp comprising the complete lactonase CDS was amplified with the primers lip2for3 and lip2rev3 (Table 2) and cloned into the pGEM-T® vector (Promega). The created vector of 4946 bp was digested with MfeI and NarI, in this way deleting 282 bp of the lactonase coding region.

The *Candida bombicola* Ura3 autotrophic marker (Van Bogaert et al., 2008a) was amplified with the primers ura3MFeIFor and ura3NarIrev (Table 2), harboring the restriction sites for, respectively, MfeI and NarI in their 5' extensions. The purified PCR fragment of 2064 bp was cut with mentioned restriction enzymes and ligated into the digested vector. The resulting vector of 6717 bp was used as a template to generate the lactonase knock-out cassette with the primers lip2for3 and lip2rev3. The fragment of 3806 bp contains the ura3 marker with approximately 0.8 kb of the lactonase sequence on each site, required for homologues recombination at the lactonase locus. This linear fragment was used to transform *Candida bombicola* PT36.

TABLE 2

Primers used for knocking out the *C. bombicola* sophorolipid lactonase gene. All primers were obtained from Sigma Genosys. Underlined regions mark restriction sites.

| Name | Feature | Sequence |
|---|---|---|
| lip2for3 | cloning lactonase | CAGCGCTGGGATTCATCTG CTC (SEQ ID NO: 3) |
| lip2rev3 | cloning lactonase | GCTAAGCAGCCTTGGGAGT TTC (SEQ ID NO: 4) |

TABLE 2-continued

Primers used for knocking out the C. bombicola sophorolipid lactonase gene. All primers were obtained from Sigma Genosys. Underlined regions mark restriction sites.

| Name | Feature | Sequence |
|---|---|---|
| ura3MFeIFor | amplification ura3 marker | TA<u>CAATTG</u>-GCCTATAAGGCTAAAGAAAGTA (SEQ ID NO: 5) |
| ura3NarIrev | amplification urea3 marker | AT<u>GGCGCC</u>-GATGCCGAGGAACTGTCATTGC (SEQ ID NO: 6) |
| koLip2FlankFor | checking 5' KO genotype | CAGACGCATTGGCTGCCTTC (SEQ ID NO: 7) |
| ura3OutBeginRev | checking 5' KO genotype | ACTGCCATCATGGTTCAACCTCAC (SEQ ID NO: 8) |
| koLip2FlankRev | checking 3' KO genotype | TACTGCTCTGCCGATCGTTG (SEQ ID NO: 9) |
| Ura3OutEndFor | checking 3' KO genotype | TAAAGAAACGAAGGGCCCAGCAGTC (SEQ ID NO: 10) |

2.1.5 Sampling

Daily sophorolipid samples were extracted as follows: 3 mL of ethanol was added to 1 mL culture broth and shaken vigorously for 5 minutes. After centrifugation at 9,000 g for 5 minutes, the supernatant was collected. At the end of the incubation period, 3 volumes ethanol were added to the culture broth for total extraction of sophorolipids. Cell debris was removed by centrifugation at 1500 g during 10 minutes.

For further gravimetric analysis, the supernatans water-ethanol mixture of the total extraction was evaporated. Two volumes of ethanol were added to dissolve the sophorolipids and the residual hydrophobic carbon source. The mixture was filtrated to remove the water-soluble compounds and was evaporated again. One volume of water was added and set at pH 7, then 1 volume of hexane was added. After vigorous shaking, the mixture was allowed to separate. The different fractions were collected, evaporated and the mass was determined. The hexane phase will contain residual oil, while the water phase contains the sophorolipids.

Samples were analyzed by HPLC and Evaporative Light Scattering Detection.

Glucose concentration in the culture supernatans was determined by analysis with the 2700 Select Biochemistry Analyzer (YSI Inc.).

Colony-forming units (CFU) were determined by plating decimal dilutions on agar plates with 10% glucose, 1% yeast extract and 0.1% urea, which were incubated at 30° C. for three days.

2.1.6 HPLC and LC-MS Analysis of Glycolipids

Sophorolipid samples were analyzed by HPLC on a Varian Prostar HPLC system using a CHROMOLITH® Performance RP-18e 100-4.6 mm column from Merck KGaA at 30° C. and Evaporative Light Scattering Detection (Alltech). A gradient of two eluents, a 0.5% acetic acid aqueous solution and acetonitrile had to be used to separate the components. The gradient started at 5% acetonitrile and linearly increased until 95% in 40 minutes. The mixture was kept this way for 10 minutes and was then brought back to 5% acetonitrile in 5 minutes. A flow rate of 1 mL/minute was applied. In order to be able to compare and quantify the different samples, dilutions of a standard were analyzed in parallel.

Liquid chromatography mass spectrometry (LCMS) analysis was performed by Intertek ASG (Manchester, UK) with a MICROMASS® QUATTRO ULTIMA™ LIMS 1107 (Waters). The detection range was set at m/z 100 to 1000 and the negative ion mode was applied. The same column and LC conditions as for the HPLC analysis were used.

2.2 Results

The lactonase knock-out cassette was constructed as described in the Materials and Methods section. This linear fragment was used to transform the ura3-negative *Candida bombicola* PT36 strain. The genotype of the transformants was checked by yeast colony PCR with two primer pairs (Table 2).

The first combination, koLip2for3 and ura3OutBeginRev, verifies the upstream recombination event; koLip2FlankFor binds the genomic DNA preceding the integration region and ura3OutBeginRev binds the marker gene of the disruption cassette. The second pair checks the downstream part in the same way: KoLip2FlankRev binds the genomic region, whereas ura3OutEndFor binds the marker gene. Several correct mutants were obtained.

If the lactonase takes part in ring closure of the acidic sophorolipids, knocking out the gene should result in a reduction of the relative amount of lactonic sophorolipids. Sophorolipid production of the knock-out was compared to the wild-type, both on medium with and without addition of rapeseed oil. Cell growth and viability were not affected; CFU for mutants were not significantly different from the wild-type and this was for the full production period. Furthermore, the glucose consumption rate was comparable to the wild-type, indicating that sophorolipid synthesis is taking place; a biochemical process consuming a lot of glucose.

During the stationary phase and at the end of the cultivation time, sophorolipid samples were collected. Surprisingly, single knock-out of the lactonase gene resulted in complete absence of any lactonic form in any sample and this was both in the supplemented and non-oil supplemented set-up (FIGS. 4A-5B). The experiments were repeated several times at different times and for the cultivations without addition of oil, between 20 and 30 g/L of sophorolipids were obtained, while, confirmed with the literature, the yield was higher when rapeseed oil was added. In this latter case, between 45 and 60 g/L were obtained.

Unexpectedly, the yields for the wild-type and the mutant were comparable. This is in contrast to previous manipulations of the sophorolipid biosynthetic pathway. Indeed, a simple knock-out of the acetyltransferase gene, leading to the production of non-acetylated sophorolipids, resulted in a production of only 5 g/L of sophorolipids, even when rapeseed oil was added (Saerens et al., 2011b). Furthermore, when aiming for the production of glucolipids by disabling the second glucosyltransferase of the sophorolipid biosynthetic pathway, a strong decrease of biosurfactant production was again observed (Saerens et al., 2011a).

As can be seen in the chromatograms of FIGS. 5A and 5B, free fatty acids derived from rapeseed oil are detected, both for the wild-type and the knock-out, meaning that the rapeseed oil triglycerides are still hydrolyzed even if an enzyme with a putative lipase function is disabled. This finding indicates that at least one other lipase enzyme is responsible for the hydrolysis of rapeseed oil triglycerides and that, consequently, rapeseed oil still can serve as a carbon source or hydrophobic substrate for sophorolipid production in the lactonase negative strain.

Example 3

Creation of a Lactonase Overexpressing C. bombicola Strain for the Production of Fully Lactonized Sophorolipids Production of a sophorolipid mixture enriched in lactonic sophorolipid molecules is obtained by the usage of a sophorolipid-producing yeast strain as a host for overexpression of the C. bombicola lactonase gene. For C. bombicola ATCC 22214, for example, an overexpression cassette is created in which the lactonase gene is under control of the constitutive and highly active GKI (phosphoglycerate kinase) promoter. These overexpression constructs are cloned into a vector already comprising the C. bombicola URA3 selection marker with up- and downstream sequences for recombination in the genome (Van Bogaert et al., 2008a) and are subsequently used for transformation of a ura3-deficient C. bombicola strain. Expressing the lactonase in this way leads to a sophorolipid mixture remarkably enriched in the lactonic forms.

3.1 Material and Methods 3.1.1 Strains and Culture Conditions; DNA Isolation and Sequencing; Transformation. See Sections 2.1.1, 2.1.2 and 2.1.3.

Other media promoting production of acidic sophorolipids such as a medium without addition of citrate were used as well.

Bioreactor experiments were carried out in a BIOSTAT® B culture vessel (Sartorius-BBI Systems) with a maximum working volume of 1.5 to 3 L. Temperature (30° C.), pH (3.5), stirring rate (800 rpm) and airflow rate (1 win) were controlled by the BIOSTAT® B control unit. 100 mL of an overnight grown shake flask culture was used to inoculate the fermentor. For maintaining pH at 3.5, 5 N NaOH was used. There was no correction for a too alkaline pH and fermentations started at pH 5.8 and were consequently allowed to drop spontaneously until 3.5. Feeding of the hydrophobic carbon source was started 48 hours after inoculation, and from then on, 25 g of rapeseed oil was added every 24 hours. Additional glucose was added 150 hours after inoculation. For the wild-type fermentations, the stirring rate had to be lowered to 600 rpm after five days of cultivation to control foam formation as the addition of the hydrophobic carbon source no longer helped.

3.1.2 Creation of the Overexpression Cassettes

The complete GKI promotor sequence was amplified from genomic DNA of Candida bombicola using the primers P124_FOR_pGKI_extinfuSpeI and P125_REV_pGKI_extlipase. The lactonase gene sequence was amplified from genomic DNA using primers P126_FOR_lipase_extpGKI and P127_REV_termlac_extInfuBamHI and both fragments were subsequently fused using fusion PCR. A vector (pGEM-t®_cassette_yEGFP) containing the URA3 auxotrophic marker (under control of its own terminator), and up- and downstream sequences for homologous recombination, was cut with the enzymes SpeI and BamHI. The abovementioned linear fragment was subsequently inserted into the cut vector using the Infusion Advantage PCR cloning kit (CLONTECH®). The resulting vector of 7896 bp is used as a template to generate the lactonase overexpression cassette with the primers P1_FOR_URA3v and P32_REV_cassette. The fragment of 4904 bp was used to transform the ura3-Candida bombicola PT36 strain and integration occurred at the ura3 locus. The resulting strain thus harbored two copies of the lactonase gene; one under its own regulatory sequences unaltered in the genome and a second one under control of the strong constitutive GKI promoter at the ura3 locus. Correct integration of the cassette at the ura3 locus was controlled by performing colony PCR with primers P33_FOR_checkcassIN and P125_REV_pGKI_extlipase at the 5' side of the insertion cassette and P35_REV_checkcassIN_DOWN and P126_FOR_lipase_extpGKI at the 3' side of the insertion cassette.

TABLE 3

Primers used for overexpression of the C. bombicola lactonase gene. All primers were obtained from Sigma Genosys.

| Name | Sequence |
| --- | --- |
| P1_FOR_URA3v | AGAACAAGGCCGAGTATGTC (SEQ ID NO: 11) |
| P32_REV_cassette | GTCAGATTAGCCTCCGACATAG (SEQ ID NO: 12) |
| P124_FOR_pGKI_extinfuSpeI | CTGGCAAATCACTAGGTGCTTA GGGTGCGTGTG (SEQ ID NO: 13) |
| P125_REV_pGKI_extlipase | GAAAAAAACAGAGCCAGCATTT TTTCTGGTTTGGAGGACCTTGG GTAG (SEQ ID NO: 14) |
| P126_FOR_lipase_extpGKI | GGTCCTCCAAACCAGAAAAAAT GCTGGCTCTGTTTTTTTCG (SEQ ID NO: 15) |
| P127_REV_termlip_ extInfuBamHI | TGCCCTGCGGGGATCTTCACTC TAAGAAATCCTCCGAGGAAATC (SEQ ID NO: 16) |
| P33_FOR_checkcassIN | CCATACTCAAGCGCGAACAC (SEQ ID NO: 34) |
| P35_REV_checkcassIN_DOWN | GAGCTCAAGACGCGTTTACTCA ATGC (SEQ ID NO: 35) |

3.1.3 Sampling

CFU and glucose were determined as described in section 2.1.5. Samples (1 mL) are withdrawn from the culture medium during cultivation and sophorolipids are extracted by addition of 440 μL ethyl acetate and 11 μL acidic acid. After vigorously shaking, the fractions are separated by centrifugation, the solvent fraction (300 μL) is diluted with 700 μL ethanol and analyzed on HPLC and Evaporative Light Scattering Detection.

Optical density (OD) of cultures was measured at 600 nm using the JASCO® V 630 bio spectrophotometer (Jasco Europe). Growth was also evaluated by determining the cell dry weight (CDW).

3.1.4 HPLC Analysis of Glycolipids

See Section 2.1.6.

3.2 Results

Three transformants were selected for further characterization and they all showed identical behavior as compared to the wild-type regarding growth and substrate consumption when cultivated on production medium. Sophorolipid production was also followed up during cultivation and results are described below.

3.2.1 Sophorolipid Production on Production Medium without Citrate

Figure 6:
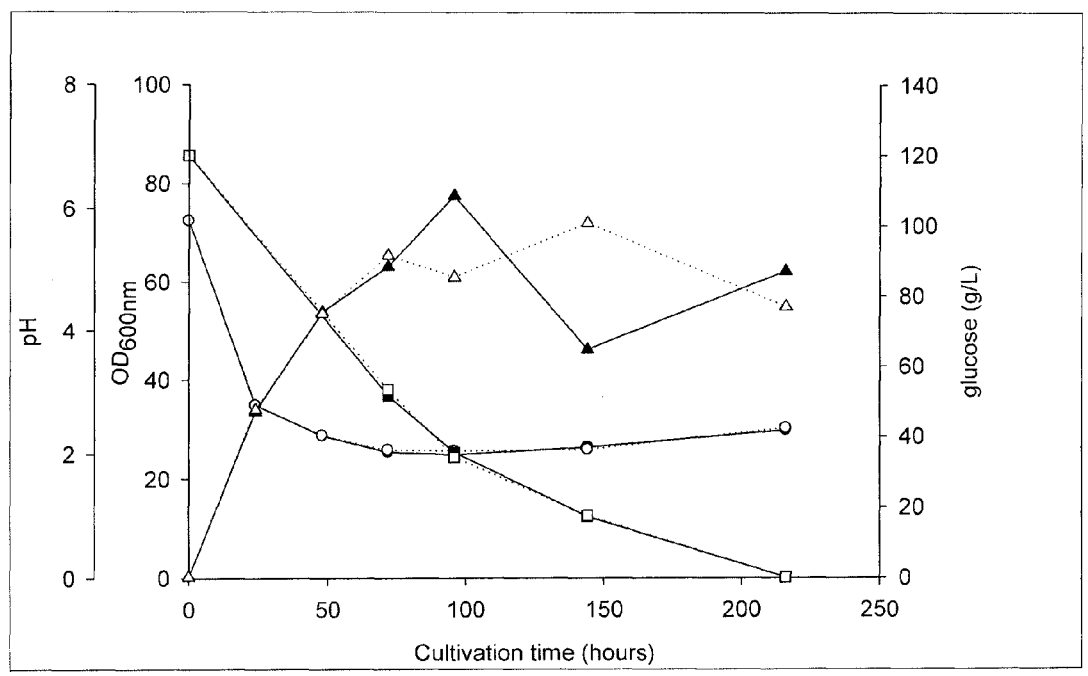
FIG. 6: Important parameters for growth and SL production of *Candida bombicola* wild-type (open) and a lipase overexpression transformant (filled) cultivated on production medium. pH (○ and ●) glucose concentration (□ and ■) and optical density (Δ and ▲) are depicted in function of time. These results are the mean of two separate experiments.

As illustrated in the background art, citrate is described to influence lactonization. Therefore, a modified production medium was used for cultivation of the wild-type and the obtained overexpression mutant. This medium did not contain citrate but was otherwise identical to the one described by Lang. pH, glucose consumption and OD are depicted in FIG. 6.

Figure 7:
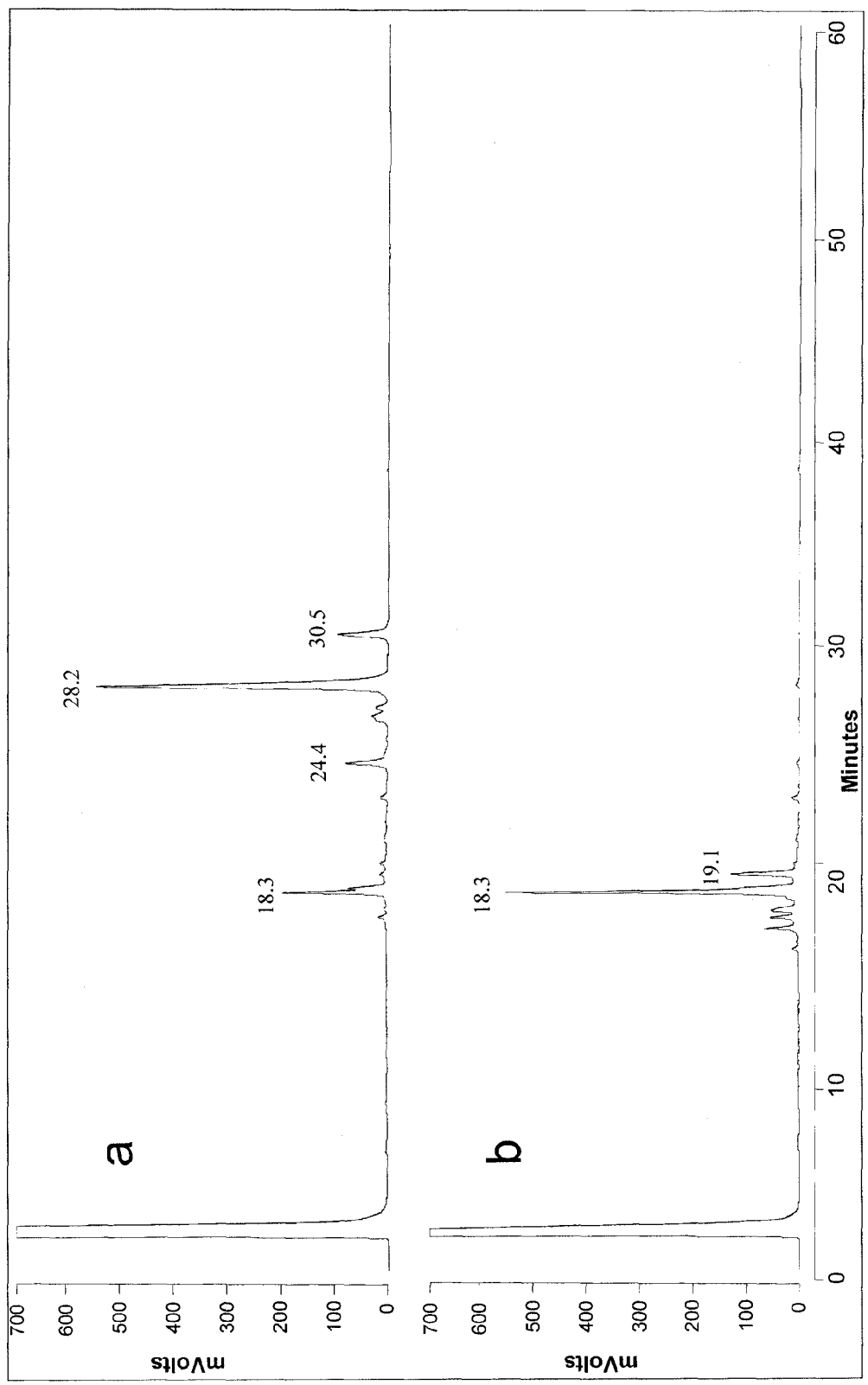
FIG. 7: HPLC-ELSD chromatograms of samples obtained from a *C. bombicola* overexpression mutant (row a) and wild-type (row b) cultivated on production medium without citrate after eight days of incubation. Samples were extracted with ethanol to not discriminate certain kinds of sophorolipids.

The observed pH drop was equal for both the wild-type and the overexpression mutant so possible differences in SL composition cannot be attributed to pH effects. Some differences in OD values were observed, but this is caused by interference of SLs and oil with the absorbance. Log CFUs were also determined before the cultures were stopped and these were equal to 8.31 and 8.41 log cfu/ml for the wild-type and the overexpression transformant, respectively. SL biosynthesis was also examined and HPLC-ELSD chromatograms are depicted in FIG. 7.

Overexpression of the lactonase gene clearly leads to lactonization of sophorolipids (peak eluting at 28.2 minutes (diacetylated lactonic) and 24.4 minutes (monoacetylated lactonic)) in the absence of citrate, which is not true for the wild-type, for which only acidic sophorolipids (peak at 18.3) are produced. These results clearly prove that the action of citrate on the lacton/acidic ratio of sophorolipids is not a result of pH as was suggested by Stüwer et al. (1987). For the wild-type, some kind of regulatory effect on the level of transcription must occur as expression of this gene from the strong, constitutive phosphoglycerate kinase promotor leads to the production of lactonic sophorolipids in the absence of citrate.

Total extractions suggested higher yields of sophorolipids for the overexpression mutant as compared to the wild-type. The total yield for the overexpression transformant was 35 g±1.3 g and 17 g±0.5 g for the wild-type, the remaining oil was equal to 0.1 g±0.0 g for the overexpression strain and 9 g±0.4 g for the wild-type.

3.2.2 Sophorolipid Production on Standard Production Medium

A second experiment was set up with the normal production medium optimized for production of lactonic sophorolipids. This was done to assess if overexpression of this already quite abundant enzyme responsible for lactonization would even lead to higher ratios of lactonic/acidic sophorolipids and possibly even higher yields of these diacetylated lactonic sophorolipids.

Figure 8:
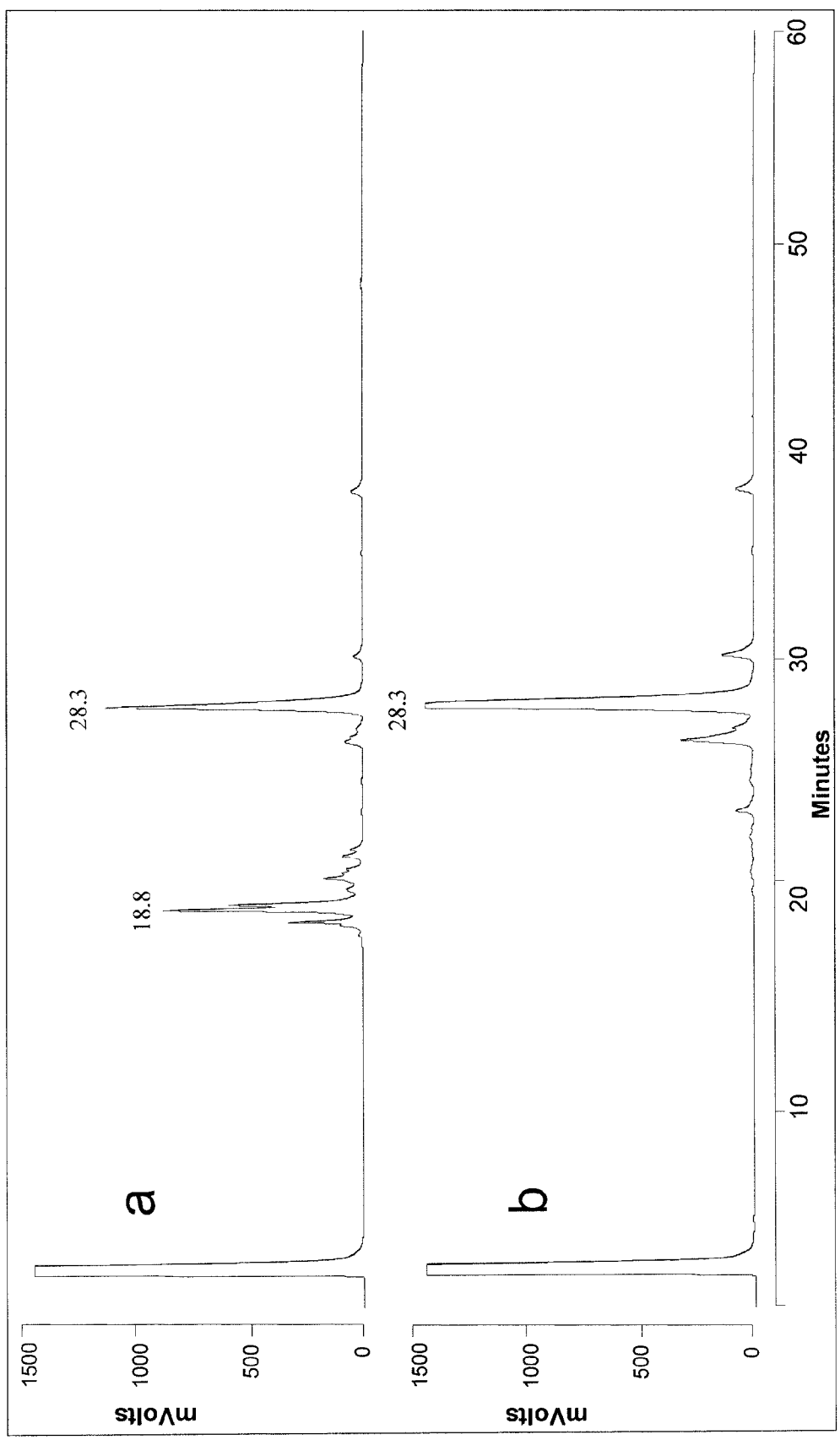
FIG. 8: HPLC-ELSD chromatograms of samples obtained from a *C. bombicola* wild-type strain (row a) and an overexpression transformant (row b) cultivated on standard production medium after eight days of incubation. Samples were extracted with ethanol to not discriminate certain kinds of SLs.
Figure 9:
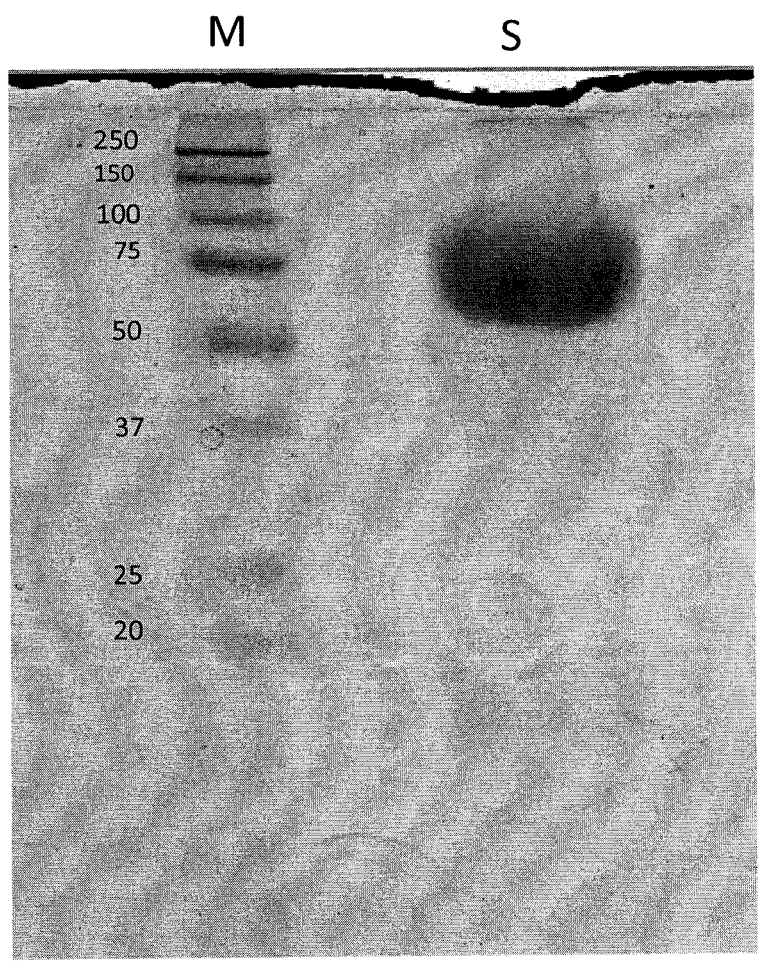
FIG. 9: SDS-PAGE representing a pooled lactonase fraction from SD 200 separation (used for analysis in 4.1.2.1). S: sample, M: marker.

Two replicas of both the wild-type and the overexpression transformant were cultivated and samples were extracted with ethanol and ethylacetate as described in the materials and methods section. HPLC-ELSD chromatograms are depicted in FIG. 8. The peak eluting at 18.8 minutes corresponds to the non-acetylated, acidic sophorolipids, whereas the peak eluting at 28.3 minutes corresponds to the diacetylated lactonic sophorolipids. Surprisingly, overexpression of the lactonase also leads to a very clear effect on sophorolipid composition on standard production medium as can be concluded when comparing FIG. 8, row a, with FIG. 8, row b. While acidic SLs are still present in substantial amounts for the wild-type, these structures are not detected for the overexpression transformant.

Total yields for these experiments were subject to high variation and it was thus decided to perform a bioreactor experiment in which all parameters can be controlled to obtain more reliable results.

3.2.3 Bioreactor Experiment on Standard Production Medium

A bioreactor with the wild-type and the lactonase overexpression mutant were run in parallel. The total SL yield of the successful wild-type cultivation accounted up to 188.74 g versus 213.42 g for the overexpression mutant. SL production was also visible earlier for the overexpression mutants and $pO_2$ dropped a lot faster for these strains. The SLs produced by the overexpression mutant were strongly enriched in the lactonic forms from the start, which confirms the results obtained in 3.2.2. At the end of the fermentation, this effect was less pronounced as lactonase expression probably occurred a lot earlier during cultivation for the overexpression mutant.

Another interesting phenomenon was the absence of foam formation for the overexpression experiments. While the wild-type stirring speed had to be adjusted to 600 rpm after five days of cultivation to prevent foam excess caused by the presence of acidic SLs, the overexpression strains could be left at the initial 800 rpm without a risk for too much foam formation. This could be an advantage for industrial applications, where foam formation can be a real burden.

Example 4

Heterologous Expression of the Lactonase Gene in *Pichia pastoris*

The lactonase of *C. bombicola* is produced extracellularly in *P. pastoris*. The recombinant protein possesses a His-tag that allows purification with a Talon column and later with a SD200 column. The Edman degradation and MS analysis were used to confirm the correctness of expressed protein sequence.

4.1 Materials and Methods
4.1.1 Recombinant Protein Production
4.1.1.1 DNA Construct Genomic DNA of *Candida bombicola* ATCC 22214 was used to pick up the mature form of the lactonase. The primers LacForvextSacII: CGTCGACTGTATGAGTTGAGT (SEQ ID NO:36) and LacRevextPstI: GCTGCAGGACTCCCTT-TAGGCC (SEQ ID NO:37) were used to create a PCR fragment with two additional restriction sites of PstI and SalI. After gel purification, the PCR product was subcloned into the pCR2.1-TOPO vector (INVITROGEN®) and propagated in *Escherichia coli* TOP10 cells (INVITROGEN®). After plasmid purification by chromatography (QIAGEN® MIDI kit), the insert was cut out with PstI and SalI. The expression vector αpPiczB (INVITROGEN®) was linearized with the same restriction enzymes and purified from the gel (innu-PREP DOUBLEpure kit). The insert was ligated to αpPiczB using T4DNA ligase and contract was transformed into one shot TOP10 electrocompetent *E. coli*. The best clone was purified with chromatography (QIAGEN®) and confirmed by multiple restriction digestion with XmnI+HindIII, NcoI and SfoI+EcoRV. Sequencing (at Beckman Coulter Genomics) confirms the αpPiczB_lac construct. The linearized αpPiczB_lac construct obtained with SacI was transformed into electrocompetent *Pichia pastoris* NRRL-Y-11430 cells.

4.1.1.2 Protein Expression

The best expressing mutant of *Pichia pastoris* NRRL-Y-11430 containing the βpPiczB_lac construct was grown in 1 L of Buffered-Glycerol Complex (BMGY) medium in two 2-L flasks containing 500 ml medium, for 48 hours at 28° C., 250 rpm. Then, BMGY medium was replaced with Buffered-Methanol Complex (BMMY) medium containing methanol instead of glycerol. The cell pellets were washed and dissolved in 1 L BMMY medium in sterile conditions. The protein expression in BMMY medium was carried for 48 hours at 28° C., 250 rpm. Every 12 hours, 1% MeOH was added for continuous stimulation of protein expression. Finally, medium containing the expressed lactonase was separated from the cells by 10 minutes centrifugation at 4000 g.

4.1.1.3 Protein Purification

The collected medium (1 L) was filtrated through a 0.22 μm bottle top filter (Corning) and divided in ten dialysis membranes with 6-8 kDa cut-off (Spectra por). The dialysis was performed in 10 L of $Na_2HPO_4$ 50 mM; NaCl 300 mM pH 7.5 buffer in 4° C. for 24 hours. Next, the dialyzed medium was pooled, filtrated through a 0.22 μm bottle top filter (Corning), and loaded on a Talon Superflow column (GE Healthcare) with a bed volume of 20 ml connected to Akta-purifier (GE Healthcare) system and equilibrated with the same buffer as used for dialysis. After loading the medium, the column was washed with equilibration buffer containing 5 mM imidazole. The His-tag protein was eluted with buffer containing 200 mM imidazole. Next, the protein was concentrated to 2 ml using VIVASPIN® columns with a MW cut-off 10 kDa (Sartorius).

The partially purified lactonase was injected into a SUPERDEX® 200 column (GE Healthcare) running in 20 mM Tris; 150 mM NaCl pH 7.5 buffer. The fractions containing the lactonase were collected and stored in −80° C.

4.1.2 Confirmation of the Lactonase Sequence

4.1.2.1 Edman Degradation

20 μL of the concentrated lactonase fraction separated by the SUPERDEX® 200 column, was further separated by 12.5% SDS-PAGE. Then, the protein was electroblotted on a PVDF membrane. N-terminal sequence determination was performed by automated Edman degradation on a Procise model 494 sequencer instrument, equipped with an on-line HPLC system consisting of a 140C Microgradient pump and a 785A programmable absorbance detector (all from Applied Biosystems). The analysis was performed with acid delivery in the gas phase.

4.1.2.2 MS Analysis

The sample from SDS-PAGE from section 4.1.2.1 was used for MS analysis. Sample preparation and analysis are described in 1.1.3., 1.1.4 and 1.1.5.

4.2 Results

The lactonase from *C. bombicola* was successfully expressed in *P. pastoris*. For efficient secretion, the original N-terminus was replaced by the α-factor secretion signal of *Saccharomyces cerevisiae* as intrinsic for the αpPiczB vector. This signal sequence is removed upon secretion by the *P. pastoris* cells. Consequently, the recombinant protein differs from the natural one: the shorter N-terminus starts with the amino acids alanine and glycine and the C-terminus contains a His-tag (see nucleic acid SEQ ID NO:32 and amino acid SEQ ID NO:33). FIG. 6 represents an SDS-PAGE with the pooled lactonase fraction from SD 200 separation (used for analysis in section 4.1.2.1). A single diffused band is visible at the height of 70-75 kDa, which is higher from the predicted MW 45 kDa of the lactonase. The shift of mass is probably due to the abundant glycosylation typical for the secreted proteins produced by *Pichia pastoris*.

SEQ ID NO: 32, nucleotides different from
SEQ ID NO: 1 are marked in bold:
GCAGGACTCCCTTTAGGCTATACTGCGGCCCCGCTGAATCATTCTATTT

TTGGCCAGAGAACATATCCAGCCTCCAAGCTGGCGAGATTTTTAGAAAAC

GGGAACTCTTAACTCTCCCAGACATCTTTGACTTTGGCCCTAATCTGGAA

AAGGTCGTACAAGTGGCTTACAAAACCCGTCTCACCGATGGCAATGACTC

GTTTTCCATCGCCAGTATCTTTATCCCTAAGAATCCAAGCCCAGAACTCA

AACTTTACTCTTATCAGACGTTTGAGGATGCCGTGCAGCTTGATTGTGCC

-continued

CCAAGCTATGCTTTAGAAGTGGGTAACAAGTCCAGCAACTATCTTCCTGT

CACTAGCAATTTATCTGCCATCAGTCGAGAACTTGAGAAAGGACGTCACT

GCATTATCCCTGATCACGAGGGCTATATTTCAGGATTCTTTGCAGGACGG

CAGGAGGGATATGCTGGTTTAGACGGAATTCGCGCTGCTCGAAACTATCT

CAATGGCACCAACGAGACCCCAATTGGTATCTTCGGATACAGTGGAGGTG

CACAAGCAACGGCCTGGATTGTTGATTTGCATGACGAGTATGCTCCTGAC

TTGAACTTTGTTGGAACAGTTTCTGGAGGCACTTTGGTTGACGCTTGGGG

CACTTTTCAGTATATCGACTATCCGAAGGTGTATCTAAAGGGCAGCATTC

TTATCATGTATACGGGTCTTTTTTCAGGTTATCCAGCTCAATTTGAGGTG

ATTTGGCCATATATTGAGCCTGTAATTCAAGAAAACATGCTACTGCTACG

TTTGGCGCCGAATGATTGTAACCAAAGCCCGATACTTCAAGGTTACAACA

ATTCAATCATGGCCGGTATACATGTGGACCTTCCCGAATTCCCTGCTTCT

AAGTACATATTCCAGCACGAGTCCCTCCTTGCCAACTACAGCGTAGTGCC

AGTTTCCACACCGAAGTTTCCTCGCTACATGTACCATGGTGGATCTGATG

AGTTGGCCAAATTGAGCCTTGTCGAGCAGTATGTTGATCAACAATGGAAT

ACCGGCGCTAATCTCACCTTCGTGGTGTATCCGGGTCTTCTTCATGACGA

GACGGCTTACCGTGGCTTTGATGCCGCGATGGATTGGCTTGATGCCCAGC

TCGATAGTGGATACCTTCCACCTGTAAACTCAACTCATACA**GTCGACCAT
CATCACCATCACCACTAG**

SEQ ID NO: 33, amino acids different
from SEQ ID NO: 2 are marked in bold:
AGLPLGYTAAPAESFYFWPENISSLQAGEIFRKRELLTLPDIFDFGPNLE

KVVQVAYKTRLTDGNDSFSIASIFIPKNPSPELKLYSYQTFEDAVQLDCA

PSYALEVGNKSSNYLPVTSNLSAISRELEKGRHCIIPDHEGYISGFFAGR

QEGYAGLDGIRAARNYLNGTNETPIGIFGYSGGAQATAWIVDLYDEYAPD

LNFVGTVSGGTLVDAWGTFQYIDYPKVYLKGSILIMYTGLFSGYPAQFEV

IWPYIEPVIQENMLLLRLAPNDCNQSPILQGYNNSIMAGIHVDLPEFPAS

KYIFQHESLLANYSVVPVSTPKFPRYMYHGGSDELAKLSLVEQYVDQQWN

TGANLTFVVYPGLLHDETAYRGFDAAMDWLDAQLDSGYLPPVNSTHT**VDH
HHHHH**

Both methods, the N-terminal sequencing and MS analysis, confirm the correctness of the recombinant lactonase. In Edman degradation, the N-terminal sequence of the lactonase was AGLPLGYTAAPA (SEQ ID NO:38), as expected for the recombinant protein (see SEQ ID NO:33). Sixteen unique peptides corresponding to the predicted sequence ID NO:33 were identified by MS analysis (Table 4).

TABLE 4

Detected peptides of the recombinant lactonase by MS analysis. Every peptide is described by sequence, its expected value and ion score as calculated by Mascot version 2.3.01.

| Nr | Score | Expect | Peptides |
|---|---|---|---|
| 1 | 42 | 6.20E-05 | K.NPSPELK.L (SEQ ID NO: 21) |

TABLE 4-continued

Detected peptides of the recombinant lactonase by MS analysis. Every peptide is described by sequence, its expected value and ion score as calculated by Mascot version 2.3.01.

| Nr | Score | Expect | Peptides |
|---|---|---|---|
| 2 | 55 | 5.80E-06 | K.VVQVAYK.T (SEQ ID NO: 22) |
| 3 | 50 | 1.00E-05 | K.VVQVAYKTR.L (SEQ ID NO: 39) |
| 4 | 81 | 1.50E-08 | R.QEGYAGLDGIR.A (SEQ ID NO: 23) |
| 5 | 46 | 2.60E-05 | R.YMYHGGSDELAK.L (SEQ ID NO: 24) |
| 6 | 64 | 3.60E-07 | R.YMYHGGSDELAK.L + Oxidation (M) (SEQ ID NO: 25) |
| 7 | 46 | 6.30E-05 | R.QEGYAGLDGIRAAR.N (SEQ ID NO: 40) |
| 8 | 91 | 1.60E-09 | K.SSNYLPVTSNLSAISR.E (SEQ ID NO: 41) |
| 9 | 73 | 8.50E-08 | K.SSNYLPVTSNLSAISR.E (SEQ ID NO: 41) |
| 10 | 83 | 1.40E-08 | R.LTDGNDSFSIASIFIPK.N (SEQ ID NO: 42) |
| 11 | 77 | 5.00E-08 | R.ELLTLPDIFDFGPNLEK.V (SEQ ID NO: 26) |
| 12 | 57 | 2.40E-06 | R.HCIIPDHEGYISGFFAGR.Q + Propionamide (C) (SEQ ID NO: 43) |
| 13 | 59 | 1.50E-06 | R.HCIIPDHEGYISGFFAGR.Q + Propionamide (C) (SEQ ID NO: 43) |
| 14 | 49 | 3.40E-05 | K.RELLTLPDIFDFGPNLEK.V (SEQ ID NO: 28) |
| 15 | 42 | 9.50E-05 | R.KRELLTLPDIFDFGPNLEK.V (SEQ ID NO: 29) |
| 16 | 70 | 1.20E-07 | R.KRELLTLPDIFDFGPNLEK.V (SEQ ID NO: 29) |
| 17 | 44 | 8.00E-05 | K.GRHCIIPDHEGYISGFFAGR.Q + Propionamide (C) (SEQ ID NO: 45) |
| 18 | 61 | 1.80E-06 | R.LTDGNDSFSIASIFIPKNPSPELK.L (SEQ ID NO: 46) |
| 19 | 43 | 7.80E-05 | R.ELLTLPDIFDFGPNLEKVVQVAYK.T (SEQ ID NO: 47) |
| 20 | 54 | 7.80E-06 | K.TRLTDGNDSFSIASIFIPKNPSPELK.L (SEQ ID NO: 48) |

Example 5

Activity Assays with Purified Lactonase

Production of the recombinant lactonase in *Pichia pastoris* allows performance of a more detailed characterization of this enzyme. First, a mixture of acidic mono-, di- and non-acetylated sophorolipids (SL) was tested to confirm that the lactonase is responsible for the SL lactone formation. Then, the different SL forms were analyzed separately to deeply investigate the enzyme behavior with those substrates. All those tests were performed at two different pH values (3.5 and 6).

The lipase/esterase activity of lactonase was investigated. The colorimetric tests were based on the release of p-nitrophenol upon hydrolysis of three p-nitrophenyl derivatives with different chain lengths, being p-nitrophenyl acetate (pnpa) and p-nitrophenyl butyrate (pnpb) (Jung and Park, 2008; Lopes et al., 2011).

5.1 Materials and Methods 5.1.1 Materials

Compounds used for enzymatic assay buffer preparation: natrium citrate, natrium hydroxide and hydrochloric acid, were purchased from Sigma.

Different types of SL were obtained by production by *C. bombicola* strains. If required, specific purification steps or chemical treatments known by the person skilled in the art were applied in order to obtain a specific form. About 100 mM stock solution in water was prepared for the enzymatic assays. Because most of the times a SL mixture was used, the average estimated molecular weight of 675.4 g/mol and a density of 1.05 g/ml were applied.

*Candida antarctica* lipase B was purchased from Sigma. The substrates pnpa and pnpb, and sodium dodecyl sulphate, TRITON® X-100, Tris as well. The solvents acetonitrile and tetrahydrofuran were received from Biosolve and Riedel de Haën, respectively. Sodium chloride was purchased from Merck.

5.1.2 Enzymatic Assays 5.1.2.1 Enzymatic Assay with Mixture of Mono-, Di-, Non-Acetylated Acidic SL 135 mg of dried SL was dissolved in 2 ml water to prepare a 100 mM stock solution used in the enzymatic assays. Five different purified protein concentrations were prepared: 0.6 µg/ml; 1.6 µg/ml; 3.2 µg/ml; 6 µg/ml; 9.2 µg/ml (stock concentration 60 µg/ml). The protein was incubated with about 5 mM of a mixture of di-, mono-, and un-acetylated acidic sophorolipids (obtained from the lactonase KO mutant) in a total volume of 1 ml. To buffer the reaction at pH 3.5 and pH 6, 50 mM $C_6H_5Na_3O_7$ was used in both cases. The assay was stopped after overnight incubation at 28° C. with rotation. For every condition, a blank reaction was prepared, where enzyme was replaced by the buffer in which enzyme was purified: 25 mM Tris, 150 mM NaCl, pH 7.5. Products from the reaction mixture were extracted with 440 µl ethylacetate and 11 µl acetic acid. From the solvent phase, 400 µl was recovered and analysis on HPLC (see section 2.1.6). The spectra from the sample and blank reaction were compared.

5.1.2.2 Enzymatic Assay with Other SL 0.6 µg/ml purified protein was incubated with ~5 mM of different SL preparations, i.e., a mix of wild-type SL; enriched lactone SL form from a standard production; pure, chemically prepared non-acetylated acidic SL and non- and mono-acetylated acidic SL produced by the KO lactonase mutant. The conditions for incubation and extraction are the same as described in 5.1.2.1.

5.1.2.3 Lipase/Esterase Activity

For the enzymatic assay with p-nitrophenyl derivates, purified lactonase in 150 mM NaCl, 25 mM Tris, pH 7.5 was used. The concentrations of the working solution, 6 mg/ml, were prepared by VIVASPIN® concentrators (Sartorius), with a MWCO of 5 KDa. The enzyme concentration was checked using a nanodrop 2000 spectrophotometer (Isogen).

*Candida Antarctica* lipase B work solutions were derived from a 1.2 mg/ml stock solution in the same enzyme buffer that was used for lactonase.

Each of the p-nitrophenyl derivates were prepared in a different way due to their stability and solubility. A work solution of 1 mM p-nitrophenyl acetate (ppna) was freshly prepared in 5% ACN/50 mM Tris, pH 7.3, just before use. For p-nitrophenyl butyrate (pnpb), a 1 mM work solution in 50 mM Tris, pH 7.3 containing 0.2% TRITON® X-100 and 0.43 M tetrahydrofuran (THF) was used.

5.1.3 Experimental Setup of the Enzyme Assay

In a 96-well microtiter plate, 200 µl of a substrate work solution was added to 40 µl of either enzyme (sample) or enzyme buffer (blank). From these wells, 200 µl was transferred to an empty well after mixing. In one scale-down experiment with lactonase, the final measured volume was only 120 Spectrofotometric measurements were performed on a Microplate reader, model 680XR (Bio-rad), using a wavelength of 405 nm, in the time drive mode, performing 60 readings with intervals of 30 or 60 seconds at an incubation temperature of 25° C. (in one experiment with lipase B, the interval between two readings was set to 15 seconds). Blanking for the background of the microtiter plate wells and/or yellowish color of the concentrated lactonase solution was done by endpoint measurements of the empty wells. Only wells with the same background were used to compare samples with blanks.

*Candida Antarctica* lipase B was used as a positive control for hydrolyses of all substrates.

5.2 Results 5.2.1 Enzymatic Assay with SL

Figure 10:
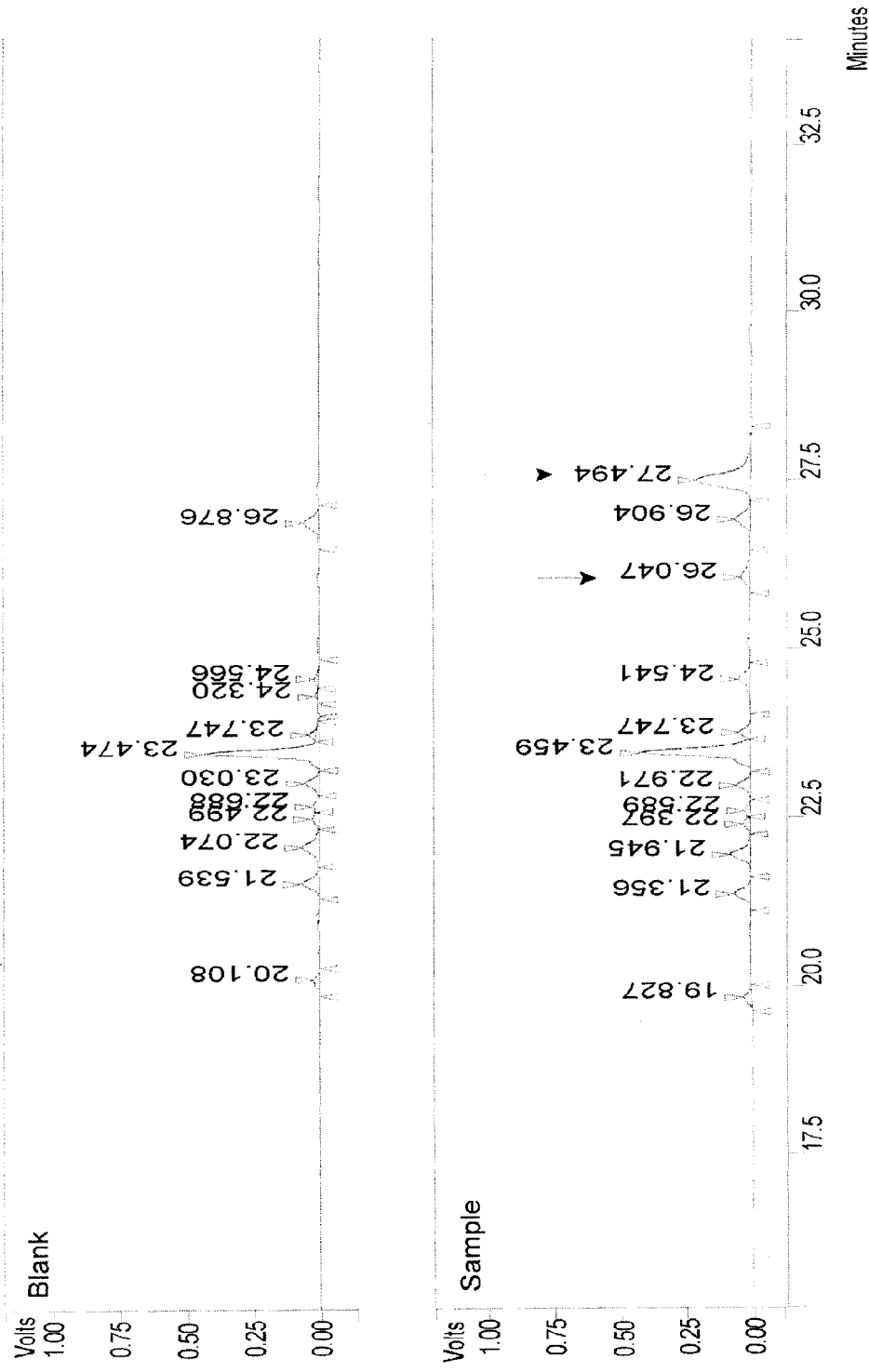
FIG. 10: HPLC chromatograms of the products extracted from the enzymatic assay with 0.6 μg/ml lactonase at pH 3.5 with a mixture of the acidic SL from the lactonase KO.
Figure 11:
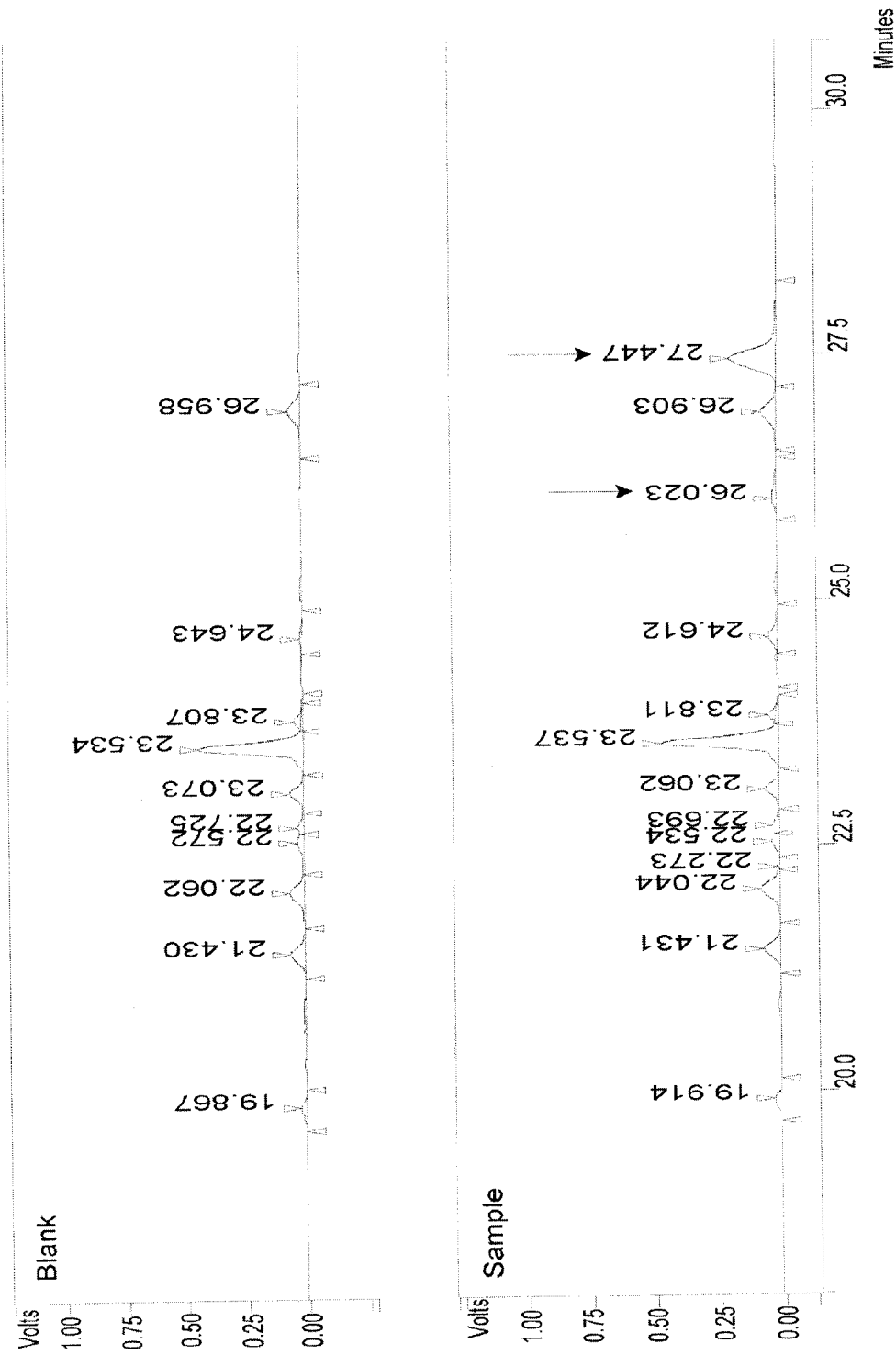
FIG. 11: HPLC chromatograms of the products extracted from the enzymatic assay with 0.6 μg/ml lactonase at pH 6 with a mixture of the acidic SL from the lactonase KO.

Extracted products after every enzymatic assay with SL were analyzed on HPLC. The chromatograms of the sample were compared with a blank experiment and new peaks were searched. FIGS. 10 and 11 present the results of the enzymatic assay at pH 3.5 and pH 6 with a mixture of mono-, di-, non-acetylated acidic SL. The black arrows mark the formed products (0.6 µg/ml lactonase): peaks eluting at 26.047 minutes and 27.494 minutes, which are not present in the blank. Those peaks correspond to the di-acetylated lactonic form of the SL with fatty acids C16 and C18:1, as determined by LC-MS (2.1.6). The same pattern was visible in assay with five different purified protein concentrations: 0.6 µg/ml; 1.6 µg/ml; 3.2 µg/ml; 6 µg/ml; and 9.2 µg/ml.

Assays were set up with non-acetylated acidic SL and mixture of non- and mono-acetylated acidic SL at pH 3.5 and pH 6. In both cases, no SL lactone form was observed. After enzymatic assays with SL mixture from WT and the enriched lactone SL mixture, no difference in the pattern between blanks and the samples were detected.

5.2.2 Colorimetric Assays

Per tested p-nitrophenyl derivative, a time drive absorption spectrum using a wavelength of 405 nm, at 25° C., was obtained.

Figure 12A:
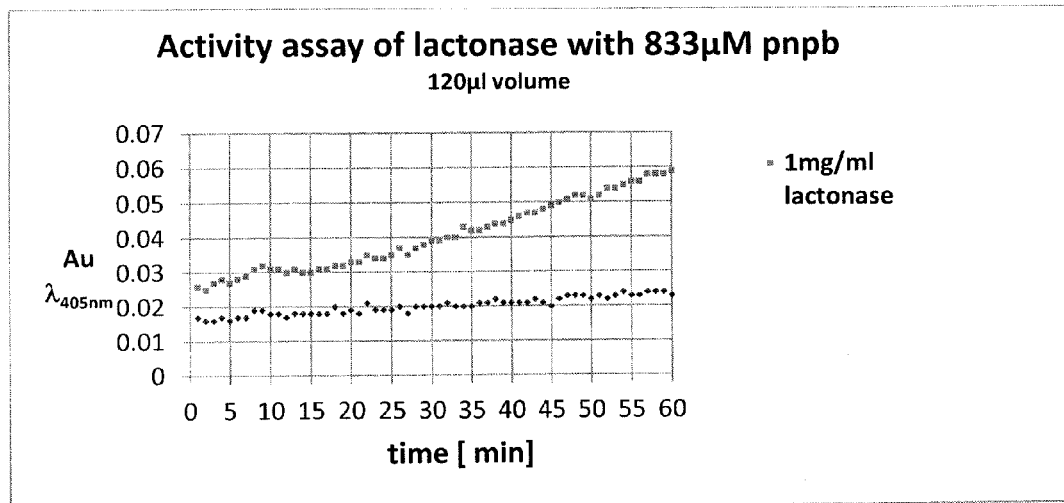
FIGS. 12A and 12B: The activity of the recombinant lactonase from *Candida bombicola* (1 mg/ml) toward p-nitrophenyl butyrate (pnpb) in a final volume of 120 μl (FIG. 12A) and 200 μl (FIG. 12B), monitored over time. Background corrections for the multi-well plate, as well as for the slightly yellowish color of the concentrated enzyme, were performed.
Figure 12B:
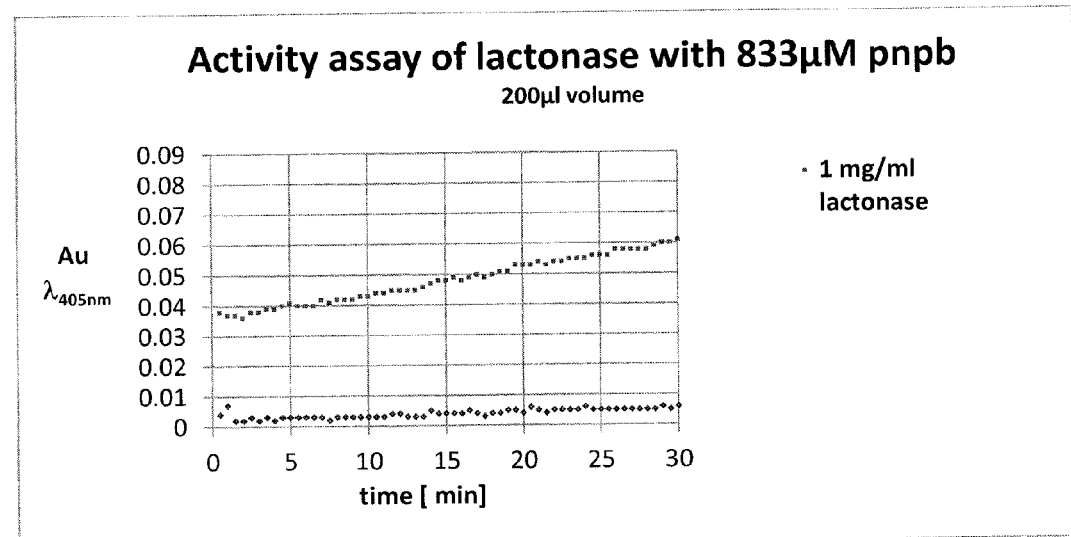

FIGS. 12A and 12B show the spectra for the 1 mg/ml lactonase in combination with p-nitrophenyl butyrate, in a final test volume set-up of, respectively, 120 and 200 µl. A slow release of p-nitrophenyl can be established, which points to some hydrolysis activity of the enzyme on the $C_4$ substrate.

Figure 13:
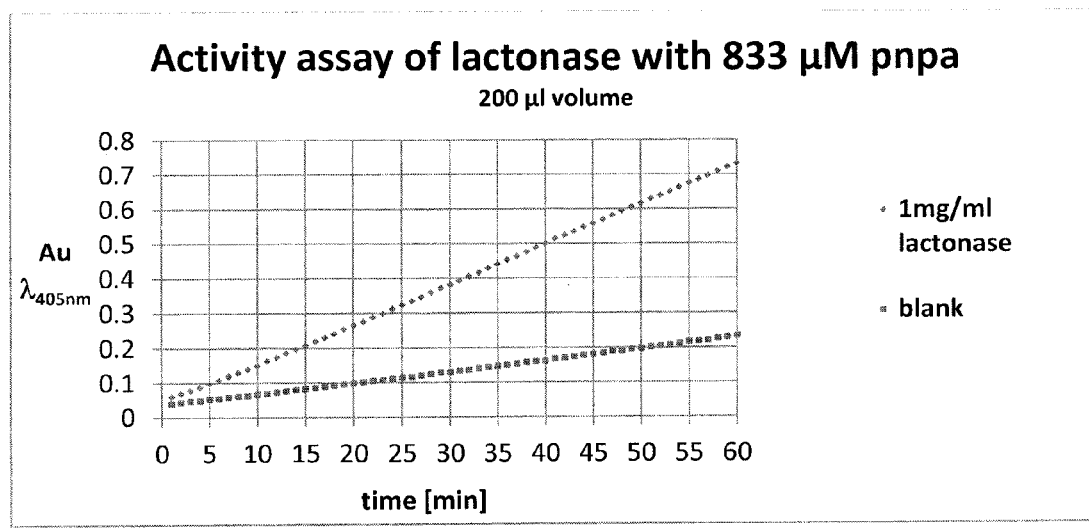
FIG. 13: The activity of the recombinant lactonase from *Candida bombicola* (1 mg/ml) over time toward p-nitrophenyl acetate (pnpa). The p-nitrophenol release in the blank is due to natural hydrolysis of (pnpa).

In the graph presented in FIG. 13, the λ405 absorption was recorded during 60 minutes for a reaction mixture containing the concentrated lactonase and p-nitrophenyl acetate. The data are corrected for background absorbance of the multi-well plate and the 1 mg/ml enzyme solution. Although natural hydrolysis causes release of p-nitrophenyl in the blank, the reaction rate clearly increases in the presence of the enzyme. Furthermore, it is obvious that the hydrolysis velocity, catalyzed by the lactonase, is higher in combination with the acetate ($C_2$) than with the butyrate ($C_4$) substrate.

The enzymatic assays with sophorolipids demonstrate that the lactonase is responsible for lactonization of the sophorolipids. After analysis of HPLC chromatograms from the enzymatic assay with different SL forms, it can be concluded that di-acetylated acidic SL are the best substrates for the lactonase. The present disclosure shows that to form a lactonic SL, preferably a low concentration of the enzyme is needed: 0.6 µg/ml. Moreover, SL lactone was produced in the assays at both pH 3.5 and pH 6, which indicates that the enzyme is active in a wide pH range.

Example 6

Mutated Lactonase 6.1 Materials and Methods 6.1.1 Mutant Design

The αpPiczB construct (INVITROGEN®) with the lactonase (sequence ID NO:32) described in section 4.1.1.1 was sent to Genscript where site-directed mutagenesis of one amino acid was performed. Ser (181) from the conservative motif GYSGGA (SEQ ID NO:44) coded by the nucleotides AGT was replaced with Ala coded by GCT.

6.1.2 Transformation, Expression and Purification

See sections 4.1.1.2 and 4.1.1.3.

6.2 Enzyme Assay 6.2.1 Enzymatic Assay with Mixture of Mono-, Di-, and Non-Acetylated Acidic SL The enzymatic assay with 5 mM mixture of mono-, di-, and non-acetylated acidic SL was performed with 6 µg/ml of lactonase and lactonase Ser mutant at pH 3.5 and pH 6.

For more details, see section 5.1.2.1.

6.3 Results and Conclusion

The enzymatic assay with mixture of mono-, di-, and non-acetylated acidic SL was identically performed for the lactonase and lactonase Ser mutant together with blanks for every condition. In the case of the non-mutated lactonase, SL lactone forms were visible in the chromatograms in both reactions at pH 3.5 and pH 6, similar to the results described in 5.2.1 and FIGS. 6 and 7. However, no product formation was visible for the enzymatic reactions with the lactonase Ser mutant.

To conclude, Ser (181) is important for the SL lactone formation.

REFERENCES

Asmer H. J., S. Lang, F. Wagner, and V. Wray (1988). Microbial production, structure elucidation and bioconversion of sophorose lipids. *J. Am. Oil Chem. Soc.* 65:1460-1466.

Azim A., V. Shah, G. F. Doncel, N. Peterson, W. Gao, and R. Gross (2006). Amino acid conjugated sophorolipids: a new family of biologically active functionalized glycolipids. *Bioconjugate Chem.* 17:1523-1529.

Banat I. M., A. Franzetti, I. Gandolfi, G. Bestetti, M. G. Martinotti, L. Fracchia, T. J. Smyth, and R. Marchant (2010). Microbial biosurfactants production, applications and future potential. *Appl. Microbiol. Biotechnol.* 87:427-444.

Bisht K. S., and R. A. Gross (1999). Enzyme-mediated regioselective acylations of sophorolipids. *J. Org. Chem.* 64:780-789.

Breithaupt T. B., and R. J. Light (1982). Affinity-chromatography and further characterization of the glucosyltransferases involved in hydroxydocosanoic acid sophoroside production in *Candida bogoriensis. J. Biol. Chem.* 257: 9622-9628.

Casas J. A., and F. Garcia-Ochoa (1999). Sophorolipid production by *Candida bombicola*: Medium composition and culture methods. *J. Biosci. Bioeng.* 88:488-494.

Chen J., X. Song, H. Zhang, Y. B. Qu, and J. Y. Miao (2006). Production, structure elucidation and anticancer properties of sophorolipid from *Wickerhamiella domercqiae*. *Enzyme Microb. Technol.* 39:501-506.

Davila A. M., R. Marchal, and J. P. Vandecasteele (1994). Sophorose lipid production from lipidic precursors—Predictive evaluation of industrial substrates. *J. Indust. Microbiol.* 13:249-257.

Davila A. M., R. Marchal, and J. P. Vandecasteele (1997). Sophorose lipid fermentation with differentiated substrate supply for growth and production phases. *Appl. Microbiol. Biotechnol.* 47:496-501.

De Graaf D. C., M. Aerts, M. Brunain, C. A. Desjardins, F. J. Jacobs, H. Werren and B. Devreese (2010). Insights into the venom composition of the ectoparasitoid wasp *Nasonia vitripennis* from bioinformatic and proteomic studies. *Insect Mol. Biol.* 19 (Suppl. 1), 11-26.

De Schutter K., and N. Callewaert (2012). *Pichia* surface display: a tool for screening single domain antibodies. *Method Mol. Biol.* 911:125-134.

Evans C. T., and C. Ratledge (1985). The physiological significance of citric acid in the control of metabolism in lipid accumulating yeasts. *Biotechnol. Gen. Engin. Rev.* 3:349-375.

Franzetti A., E. Tamburini, and I. M. Banat (2010). Applications of biological surface active compounds in remediation technologies. In *Advances in Experimental medicine and biology* Volume 672. Ramkrishna S (ed). Springer-Verlag Berlin: Germany; 121-134.

Garcia-Ochoa F., and J. A. Casas (1999). Unstructured kinetic model for sophorolipid production by *Candida bombicola*. *Enzyme Microb. Technol.* 25:613-621.

Gorin P. A. J., J. F. T. Spencer, and A. P. Tulloch (1961). Hydroxy fatty acid glycosides of sophorose from *Torulopsis magnoliae*. *Can. J. Chem.* 39:846-855.

Hommel R. K., L. Weber, A. Weiss, U. Himmelreich, O. Rilke, and H. P. Kleber (1994). Production of sophorose lipid by *Candida* (*Torulopsis*) *apicola* grown on glucose. *J. Biotechnol.* 33:147-155.

Hu Y. M., and L. K. Ju (2001b). Sophorolipid production from different lipid precursors observed with LC-MS. *Enzyme Microbial. Technol.* 29:593-601.

Imura T., Y. Masuda, H. Minamikawa, T. Fukuoka, M. Konishi, T. Morita, H. Sakai, M. Abe and D. Kitamoto (2010). Enzymatic conversion of unacetylated sophorose lipid into acetylated glucose lipid: surface-active properties of novel bolaform biosurfactants. *J. Oleo. Sci.* 59:495-501.

Inoue H., H. Nojima, and H. Okayama (1990). High efficiency transformation of *Escherichia coli* with plasmids. *Gene* 96:23-28.

Jung S., and S. Park (2008). Improving the expression yield of *Candida Antarctica* lipase B in *Escherichia coli* by mutagenesis. *Biotechnol. Lett.* 30:717-722.

Kasture M., S. Singh, P. Patel, P. A. Joy, A. A. Prabhun, C. B. Ramana, and B. L. V. Prasad (2007). Multi-utility sophorolipids as nanoparticle capping agents: synthesis of stable and water-dispersible co-nanoparticles. *Langmuir* 23:11409-11412.

Konishi M., T. Fukuoka, T. Morita, T. Imura, and D. Kitamoto (2008). Production of new types of sophorolipids by *Candida batistae*. *J. Oleo. Sci.* 57:359-369.

Kralova I., and J. Sjoblom (2009). Surfactants used in food industry: a review. *J. Disper. Sci. Technol.* 30:1363-1383.

Kurtzman C. P., N. P. J. Price, K. J. Ray, and T. M. Kuo (2010). Production of sophorolipid biosurfactants by multiple species of the *Starmerella* (*Candida*) *bombicola* yeast Glade. *FEMS Microbiol. Lett.* 311:140-146.

Lang S., A. Brakemeier, R. Heckmann, S. Spöckner, and U. Rau (2000). Production of native and modified sophorose lipids. *Chim. Oggi*. 18:76-79.

Lopes D. B., L. P. Fraga, L. F. Fleuri, and G. A. Macedo (2011). Lipase and esterase—to what extent can this classification be applied accurately? *Cienc. Tecnol. Aliment. Campinas.* 31:608-613.

Mulligan C. N. (2009). Recent advances in the environmental applications of biosurfactants. *Curr. Opin. Colloid. In.* 14:372-378.

Nunez A., T. A. Foglia, and R. Ashby (2003). Enzymatic synthesis of a galactopyranose sophorolipid fatty acid-ester. *Biotechnol. Lett.* 25:1291-1297.

Rappsilber J., U. Ryder, A. I. Lamond, and M. Mann (2002). Large-scale proteomic analysis of the human spliceosome. *Genome res.* 12:1231-1245.

Rau U., S. Hammen, R. Heckmann, V. Wray, and S. Lang (2001). Sophorolipids: a source for novel compounds. *Ind. Crop. Prod.* 13:85-92.

Saerens K., I. Van Bogaert, W. Soetaert, E. J. Vandamme (2009). Production of glucolipids and specialty fatty acids from sophorolipids by *Penicillium decumbens naringinase*: Optimization and kinetics. *Biotechnol. J.* 4:517-524.

Saerens K. M. J., S. Roelants, I. N. A. Van Bogaert, and W. Soetaert (2011a). Identification of the UDP-glucosyltransferase gene UGTA1, responsible for the first glucosylation step in the sophorolipid biosynthetic pathway of *Candida bombicola* ATCC22214. *FEMS Yeast Res.* 11:123-132.

Saerens K., S. Saey, and W. Soetaert (2011b). One-step production of unacetylated sophorolipids by an acetyltransferase negative *Candida bombicola*. *Biotechnol. Bioengin.* 108:2923-2931.

Saerens K., J. Zhang, L. Saey, I. N. Van Bogaert, and W. Soetaert (2011c). Cloning and functional characterization of the UDP-glucosyltransferase UgtB1 involved in sophorolipid production by *Candida bombicola* and creation of a glucolipid-producing yeast strain. *Yeast* 28:279-292.

Spencer J. F. T., P. A. J. Gorin, and A. P. Tulloch (1970). *Torulopsis bombicola* sp. n. *A Van Leeuw. J. Microb. Ser.* 36:129-133.

Stüwer O., R. Hommel, D. Haferburg, and H. P. Kleber (1987). Production of crystalline surface-active glycolipids by a strain of *Torulopsis apicola*. *J. Biotechnol.* 6:259-269.

Tulloch A. P., J. F. T. Spencer, and M. H. Deinema (1968a). A new hydroxy fatty acid sophoroside from *Candida bogoriensis*. *Can. J. Chem.* 46:345-348.

Van Bogaert I. N. A., S. L. De Maeseneire, D. Develter, W. Soetaert, and E. J. Vandamme (2008a). Development of a transformation and selection system for the glycolipid producing yeast *Candida bombicola*. *Yeast* 25:272-278.

Van Bogaert I. N. A., J. Zhang, and W. Soetaert (2011). Microbial synthesis of sophorolipids. *Process Biochem.* 46:821-833.

Winkler U. K., and M. Stuckmann (1979). Glycogen, Hyaluronate, and Some Other Polysaccharides Greatly Enhance the Formation of Exolipase by *Serratiamarcescens*. *J. Bacteriol.* 138:663-70.

Zerkowski J. A., and D. K. Y. Solaiman (2007). Polyhydroxy fatty acids derived from sophorolipids. *J. Amer. Oil Chem. Soc.* 84:463-471.

Zerkowski J. A., D. K. Y. Solaiman, R. D. Ashby, and T. A. Foglia (2006). Head group-modified sophorolipids: synthesis of new cationic, zwitterionic, and anionic surfactants. *J. Surfactants Deterg.* 9:57-62.

The invention claimed is:

1. A method of lactonizing or polymerizing carbohydrate-containing compounds, lipids, fatty acids, hydroxylated fatty acids, alcohols, dicarboxylic acids, or mixtures thereof, the method comprising:
utilizing a polypeptide comprising SEQ ID NO:33 to lactonize or to polymerize the carbohydrate-containing compounds, lipids, fatty acids, hydroxylated fatty acids, alcohols, dicarboxylic acids or mixtures thereof.

2. The method according to claim 1, wherein said carbohydrate-containing compounds are sophorolipids.

3. A method of lactonizing or polymerizing carbohydrate-containing compounds, lipids, fatty acids, hydroxylated fatty acids, alcohols, dicarboxylic acids or mixtures thereof, the method comprising:
contacting a polypeptide comprising SEQ ID NO:33 with the carbohydrate-containing compounds, lipids, fatty acids, hydroxylated fatty acids, alcohols, dicarboxylic acids or mixtures thereof to lactonize or polymerize the carbohydrate-containing compounds, lipids, fatty acids, hydroxylated fatty acids, alcohols, dicarboxylic acids or mixtures thereof.

4. A method of lactonizing or polymerizing carbohydrate-containing compounds, lipids, fatty acids, hydroxylated fatty acids, alcohols, dicarboxylic acids, or mixtures thereof, the method comprising:
utilizing a polypeptide comprising SEQ ID NO:2, SEQ ID NO:33, or a peptide having at least 98% sequence identity with SEQ ID NO:2 or SEQ ID NO:33 and having lactonase activity to lactonize or to polymerize the carbohydrate-containing compounds, lipids, fatty acids, hydroxylated fatty acids, alcohols, dicarboxylic acids or mixtures thereof.

5. The method according to claim 4, wherein the polypeptide comprises SEQ ID NO:2.

6. A method of lactonizing or polymerizing carbohydrate-containing compounds, lipids, fatty acids, hydroxylated fatty acids, alcohols, dicarboxylic acids or mixtures thereof, the method comprising:
contacting a polypeptide comprising SEQ ID NO:2, SEQ ID NO:33, or a peptide having at least 98% sequence identity with SEQ ID NO:2 or SEQ ID NO:33 and having lactonase activity with the carbohydrate-containing compounds, lipids, fatty acids, hydroxylated fatty acids, alcohols, dicarboxylic acids or mixtures thereof with the polypeptide, fragment or variant thereof to lactonize or polymerize the carbohydrate-containing compounds, lipids, fatty acids, hydroxylated fatty acids, alcohols, dicarboxylic acids or mixtures thereof.

7. The method according to claim 6, wherein the polypeptide comprises SEQ ID NO:2.

* * * * *

```
                        SEQUENCE LISTING

<160> NUMBER OF SEQ ID NOS: 48

<210> SEQ ID NO 1
<211> LENGTH: 1233
<212> TYPE: DNA
<213> ORGANISM: Candida bombicola

<400> SEQUENCE: 1
atgctggctc tgttttttc gcttgcgcct ctactttctc aagctctccc tttaggctat      60
actgcggccc ccgctgaatc attctatttt tggccagaga acatatccag cctccaagct    120
ggcgagattt ttagaaaacg ggaactctta actctcccag acatctttga ctttggcct     180 aatctggaaa aggtcgtaca agtggcttac aaaacccgtc tcaccgatgg caatgactcg    240
ttttccatcg ccagtatctt tatccctaag aatccaagcc cagaactcaa actttactct    300
tatcagacgt tgaggatgc cgtgcagctt gattgtgccc caagctatgc tttagaagtg     360
ggtaacaagt ccagcaacta tcttcctgtc actagcaatt tatctgccat cagtcgagaa    420
cttgagaaag gacgtcactg cattatccct gatcacgagg gctatatttc aggattcttt    480
gcaggacggc aggagggata tgctggttta acggaattc gcgctgctcg aaactatctc     540
aatggcacca acgagacccc aattggtatc ttcggataca gtggaggtgc acaagcaacg    600
gcctggattg ttgatttgca tgacgagtat gctcctgact gaactttgt tggaacagtt     660 tctggaggca ctttggttga cgcttggggc acttttcagt atatcgacta tccgaaggtg    720
tatctaaagg gcagcattct tatcatgtat acgggtcttt tttcaggtta tccagctcaa    780
tttgaggtga tttggccata tattgagcct gtaattcaag aaaacatgct actgctacgt    840
ttggcgccga atgattgtaa ccaaagcccg atacttcaag gttacaacaa ttcaatcatg    900
gccggtatac atgtggacct tcccgaattc cctgcttcta agtacatatt ccagcacgag    960
tccctccttg ccaactacag cgtagtgcca gtttccacac cgaagtttcc tcgctacatg   1020
taccatggtg gatctgatga gttggccaaa ttgagccttg tcgagcagta tgttgatcaa   1080
caatggaata ccggcgctaa tctcaccttc gtggtgtatc cgggtcttct tcatgacgag   1140
acggcttacc gtggctttga tgccgcgatg gattggctta tgcccagct cgatagtgga    1200 taccttccac ctgtaaactc aactcataca tga                                1233

<210> SEQ ID NO 2
<211> LENGTH: 410
<212> TYPE: PRT
<213> ORGANISM: Candida bombicola

<400> SEQUENCE: 2

Met Leu Ala Leu Phe Phe Ser Leu Ala Pro Leu Leu Ser Gln Ala Leu
1               5                   10                  15

Pro Leu Gly Tyr Thr Ala Ala Pro Ala Glu Ser Phe Tyr Phe Trp Pro
            20                  25                  30

Glu Asn Ile Ser Ser Leu Gln Ala Gly Glu Ile Phe Arg Lys Arg Glu
        35                  40                  45

Leu Leu Thr Leu Pro Asp Ile Phe Asp Phe Gly Pro Asn Leu Glu Lys
    50                  55                  60

Val Val Gln Val Ala Tyr Lys Thr Arg Leu Thr Asp Gly Asn Asp Ser
65                  70                  75                  80

Phe Ser Ile Ala Ser Ile Phe Ile Pro Lys Asn Pro Ser Pro Glu Leu
```

```
            85                  90                  95
Lys Leu Tyr Ser Tyr Gln Thr Phe Glu Asp Ala Val Gln Leu Asp Cys
            100                 105                 110

Ala Pro Ser Tyr Ala Leu Glu Val Gly Asn Lys Ser Ser Asn Tyr Leu
            115                 120                 125

Pro Val Thr Ser Asn Leu Ser Ala Ile Ser Arg Glu Leu Glu Lys Gly
    130                 135                 140

Arg His Cys Ile Ile Pro Asp His Glu Gly Tyr Ile Ser Gly Phe Phe
145                 150                 155                 160

Ala Gly Arg Gln Glu Gly Tyr Ala Gly Leu Asp Gly Ile Arg Ala Ala
                165                 170                 175

Arg Asn Tyr Leu Asn Gly Thr Asn Glu Thr Pro Ile Gly Ile Phe Gly
                180                 185                 190

Tyr Ser Gly Gly Ala Gln Ala Thr Ala Trp Ile Val Asp Leu His Asp
                195                 200                 205

Glu Tyr Ala Pro Asp Leu Asn Phe Val Gly Thr Val Ser Gly Gly Thr
210                 215                 220

Leu Val Asp Ala Trp Gly Thr Phe Gln Tyr Ile Asp Tyr Pro Lys Val
225                 230                 235                 240

Tyr Leu Lys Gly Ser Ile Leu Ile Met Tyr Thr Gly Leu Phe Ser Gly
                245                 250                 255

Tyr Pro Ala Gln Phe Glu Val Ile Trp Pro Tyr Ile Glu Pro Val Ile
                260                 265                 270

Gln Glu Asn Met Leu Leu Leu Arg Leu Ala Pro Asn Asp Cys Asn Gln
                275                 280                 285

Ser Pro Ile Leu Gln Gly Tyr Asn Asn Ser Ile Met Ala Gly Ile His
    290                 295                 300

Val Asp Leu Pro Glu Phe Pro Ala Ser Lys Tyr Ile Phe Gln His Glu
305                 310                 315                 320

Ser Leu Leu Ala Asn Tyr Ser Val Val Pro Val Ser Thr Pro Lys Phe
                325                 330                 335

Pro Arg Tyr Met Tyr His Gly Gly Ser Asp Glu Leu Ala Lys Leu Ser
                340                 345                 350

Leu Val Glu Gln Tyr Val Asp Gln Gln Trp Asn Thr Gly Ala Asn Leu
                355                 360                 365

Thr Phe Val Val Tyr Pro Gly Leu Leu His Asp Glu Thr Ala Tyr Arg
            370                 375                 380

Gly Phe Asp Ala Ala Met Asp Trp Leu Asp Ala Gln Leu Asp Ser Gly
385                 390                 395                 400

Tyr Leu Pro Pro Val Asn Ser Thr His Thr
                405                 410

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
cagcgctggg attcatctgc tc                                        22

<210> SEQ ID NO 4
<211> LENGTH: 22
<212> TYPE: DNA
<213> ORGANISM: Artificial sequence
```

```
<220> FEATURE:
<223> OTHER INFORMATION: Primer

<400> SEQUENCE: 4
gctaagcagc cttgggagtt tc                                              22

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5
tacaattggc ctataaggct aaagaaagta                                      30

<210> SEQ ID NO 6
<211> LENGTH: 30
<212> TYPE: DNA
<213> ORGANISM: Artificial sequence
<220> FEATURE:
<223> OTHER INFORMATION: Primer

<400> SEQUENCE: 6
atggcgccga tgccgaggaa ctgtcattgc                                      30

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
cagacgcatt ggctgccttc                                                 20

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
actgccatca tggttcaacc tcac                                            24

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
tactgctctg ccgatcgttg                                                 20

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10
taaagaaacg aagggcccag cagtc                                           25
```

```
<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
agaacaaggc cgagtatgtc                                              20

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
gtcagattag cctccgacat ag                                           22

<210> SEQ ID NO 13
<211> LENGTH: 33
<212> TYPE: DNA
<213> ORGANISM: Artificial sequence
<220> FEATURE:
<223> OTHER INFORMATION: Primer

<400> SEQUENCE: 13
ctggcaaatc actaggtgct tagggtgcgt gtg                               33

<210> SEQ ID NO 14
<211> LENGTH: 48
<212> TYPE: DNA
<213> ORGANISM: Artificial sequence
<220> FEATURE:
<223> OTHER INFORMATION: Primer

<400> SEQUENCE: 14
gaaaaaaaca gagccagcat tttttctggt ttggaggacc ttgggtag               48

<210> SEQ ID NO 15
<211> LENGTH: 41
<212> TYPE: DNA
<213> ORGANISM: Artificial sequence
<220> FEATURE:
<223> OTHER INFORMATION: Primer

<400> SEQUENCE: 15
ggtcctccaa accagaaaaa atgctggctc tgttttttc g                       41

<210> SEQ ID NO 16
<211> LENGTH: 44
<212> TYPE: DNA
<213> ORGANISM: Artificial sequence
<220> FEATURE:
<223> OTHER INFORMATION: Primer

<400> SEQUENCE: 16
tgccctgcgg ggatcttcac tctaagaaat cctccgagga aatc                   44

<210> SEQ ID NO 17
<211> LENGTH: 121
<212> TYPE: DNA
<213> ORGANISM: Artificial sequence
<220> FEATURE:
<223> OTHER INFORMATION: Primer
```

-continued

```
<400> SEQUENCE: 17
cagcactggc cgatacccaa agtatataat gcgccgttga acggttatag tcggtcaagc      60
tcttaaagaa agacttaaca acaaaaacaa ctctacacaa atgctggctc tgttttttc      120 g                                                                      121

<210> SEQ ID NO 18
<211> LENGTH: 117
<212> TYPE: DNA
<213> ORGANISM: Artificial sequence
<220> FEATURE:
<223> OTHER INFORMATION: Primer

<400> SEQUENCE: 18
cattgcaggg tgtgcgtcta cgatataaca cgatcgacat cgcgctgggt atgcttctgg      60
gtaaggggtc gcaacgtgtg agttgtcagc actggccgat acccaaagta tataatg        117

<210> SEQ ID NO 19
<211> LENGTH: 116
<212> TYPE: DNA
<213> ORGANISM: Artificial sequence
<220> FEATURE:
<223> OTHER INFORMATION: Primer

<400> SEQUENCE: 19
acaagttttt aacatgggtt ttgatttata ttgttttata tgagcgcctc acatatgcgc      60
tgacagccta ttaggagaaa ttcatgtatg agttgagttt acaggtggaa ggtatc         116

<210> SEQ ID NO 20
<211> LENGTH: 120
<212> TYPE: DNA
<213> ORGANISM: Artificial sequence
<220> FEATURE:
<223> OTHER INFORMATION: Primer

<400> SEQUENCE: 20
gactttggtc gatatgacga gaatcaggca ataatagctt aagctgaagt gttttagat      60 ttagttcgga gtgcgcttct caaaagtgct gggatcaaca agttttaac atgggttttg     120

<210> SEQ ID NO 21
<211> LENGTH: 9
<212> TYPE: PRT
<213> ORGANISM: Candida bombicola

<400> SEQUENCE: 21

Lys Asn Pro Ser Pro Glu Leu Lys Leu
1               5

<210> SEQ ID NO 22
<211> LENGTH: 9
<212> TYPE: PRT
<213> ORGANISM: Candida bombicola

<400> SEQUENCE: 22

Lys Val Val Gln Val Ala Tyr Lys Thr
1               5

<210> SEQ ID NO 23
<211> LENGTH: 13
<212> TYPE: PRT
<213> ORGANISM: Candida bombicola
```

<400> SEQUENCE: 23

Arg Gln Glu Gly Tyr Ala Gly Leu Asp Gly Ile Arg Ala
1               5                   10

<210> SEQ ID NO 24
<211> LENGTH: 14
<212> TYPE: PRT
<213> ORGANISM: Candida bombicola

<400> SEQUENCE: 24

Arg Tyr Met Tyr His Gly Gly Ser Asp Glu Leu Ala Lys Leu
1               5                   10

<210> SEQ ID NO 25
<211> LENGTH: 14
<212> TYPE: PRT
<213> ORGANISM: Candida bombicola

<400> SEQUENCE: 25

Arg Tyr Met Tyr His Gly Gly Ser Asp Glu Leu Ala Lys Leu
1               5                   10

<210> SEQ ID NO 26
<211> LENGTH: 19
<212> TYPE: PRT
<213> ORGANISM: Candida bombicola

<400> SEQUENCE: 26

Arg Glu Leu Leu Thr Leu Pro Asp Ile Phe Asp Phe Gly Pro Asn Leu
1               5                   10                  15

Glu Lys Val

<210> SEQ ID NO 27
<211> LENGTH: 19
<212> TYPE: PRT
<213> ORGANISM: Candida bombicola

<400> SEQUENCE: 27

Arg Glu Leu Leu Thr Leu Pro Asp Ile Phe Asp Phe Gly Pro Asn Leu
1               5                   10                  15

Glu Lys Val

<210> SEQ ID NO 28
<211> LENGTH: 20
<212> TYPE: PRT
<213> ORGANISM: Candida bombicola

<400> SEQUENCE: 28

Lys Arg Glu Leu Leu Thr Leu Pro Asp Ile Phe Asp Phe Gly Pro Asn
1               5                   10                  15

Leu Glu Lys Val
            20

<210> SEQ ID NO 29
<211> LENGTH: 21
<212> TYPE: PRT
<213> ORGANISM: Candida bombicola

<400> SEQUENCE: 29

Arg Lys Arg Glu Leu Leu Thr Leu Pro Asp Ile Phe Asp Phe Gly Pro
1               5                   10                  15

Asn Leu Glu Lys Val

<210> SEQ ID NO 30
<211> LENGTH: 27
<212> TYPE: DNA
<213> ORGANISM: Artificial sequence
<220> FEATURE:
<223> OTHER INFORMATION: Primer

<400> SEQUENCE: 30

```
cccgcggatg ctggctctgt tttttc                                        27
```

<210> SEQ ID NO 31
<211> LENGTH: 39
<212> TYPE: DNA
<213> ORGANISM: Artificial sequence
<220> FEATURE:
<223> OTHER INFORMATION: Primer

<400> SEQUENCE: 31

```
ttctagatgt atgagttgag tttacaggtg aaggtatc                           39
```

<210> SEQ ID NO 32
<211> LENGTH: 1218
<212> TYPE: DNA
<213> ORGANISM: Candida bombicola

<400> SEQUENCE: 32

```
gcaggactcc ctttaggcta tactgcggcc cccgctgaat cattctattt ttggccagag    60
aacatatcca gcctccaagc tggcgagatt tttagaaaac gggaactctt aactctccca   120
gacatctttg actttggccc taatctggaa aaggtcgtac aagtggctta caaaacccgt   180
ctcaccgatg gcaatgactc gttttccatc gccagtatct ttatccctaa gaatccaagc   240
ccagaactca aactttactc ttatcagacg tttgaggatg ccgtgcagct tgattgtgcc   300
ccaagctatg ctttagaagt gggtaacaag tccagcaact atcttcctgt cactagcaat   360
ttatctgcca tcagtcgaga acttgagaaa ggacgtcact gcattatccc tgatcacgag   420
ggctatattt caggattctt tgcaggacgg caggagggat atgctggttt agacggaatt   480
cgcgctgctc gaaactatct caatggcacc aacgagaccc caattggtat cttcggatac   540
agtggaggtg cacaagcaac ggcctggatt gttgatttgc atgacgagta tgctcctgac   600
ttgaactttg ttggaacagt ttctggaggc actttggttg acgcttgggg cactttttcag  660
tatatcgact atccgaaggt gtatctaaag ggcagcattc ttatcatgta tacgggtctt   720
ttttcaggtt atccagctca atttgaggtg atttggccat atattgagcc tgtaattcaa   780
gaaaacatgc tactgctacg tttggcgccg aatgattgta accaaagccc gatacttcaa   840
ggttacaaca attcaatcat ggccggtata catgtggacc ttcccgaatt ccctgcttct   900
aagtacatat tccagcacga gtccctcctt gccaactaca gcgtagtgcc agtttccaca   960
ccgaagtttc ctcgctacat gtaccatggt ggatctgatg agttggccaa attgagcctt  1020
gtcgagcagt atgttgatca acaatggaat accggcgcta atctcacctt cgtggtgtat  1080
ccgggtcttc ttcatgacga gacggcttac cgtggctttg atgccgcgat ggattggctt  1140
gatgcccagc tcgatagtgg ataccttcca cctgtaaact caactcatac agtcgaccat  1200
catcaccatc accactag                                               1218
```

<210> SEQ ID NO 33
<211> LENGTH: 405

<212> TYPE: PRT
<213> ORGANISM: Candida bombicola

<400> SEQUENCE: 33

```
Ala Gly Leu Pro Leu Gly Tyr Thr Ala Ala Pro Ala Glu Ser Phe Tyr
1               5                   10                  15

Phe Trp Pro Glu Asn Ile Ser Ser Leu Gln Ala Gly Glu Ile Phe Arg
            20                  25                  30

Lys Arg Glu Leu Leu Thr Leu Pro Asp Ile Phe Asp Phe Gly Pro Asn
                35                  40                  45

Leu Glu Lys Val Val Gln Val Ala Tyr Lys Thr Arg Leu Thr Asp Gly
            50                  55                  60

Asn Asp Ser Phe Ser Ile Ala Ser Ile Phe Ile Pro Lys Asn Pro Ser
65                  70                  75                  80

Pro Glu Leu Lys Leu Tyr Ser Tyr Gln Thr Phe Glu Asp Ala Val Gln
                85                  90                  95

Leu Asp Cys Ala Pro Ser Tyr Ala Leu Glu Val Gly Asn Lys Ser Ser
            100                 105                 110

Asn Tyr Leu Pro Val Thr Ser Asn Leu Ser Ala Ile Ser Arg Glu Leu
        115                 120                 125

Glu Lys Gly Arg His Cys Ile Ile Pro Asp His Glu Gly Tyr Ile Ser
130                 135                 140

Gly Phe Phe Ala Gly Arg Gln Glu Gly Tyr Ala Gly Leu Asp Gly Ile
145                 150                 155                 160

Arg Ala Ala Arg Asn Tyr Leu Asn Gly Thr Asn Glu Thr Pro Ile Gly
                165                 170                 175

Ile Phe Gly Tyr Ser Gly Gly Ala Gln Ala Thr Ala Trp Ile Val Asp
            180                 185                 190

Leu Tyr Asp Glu Tyr Ala Pro Asp Leu Asn Phe Val Gly Thr Val Ser
        195                 200                 205

Gly Gly Thr Leu Val Asp Ala Trp Gly Thr Phe Gln Tyr Ile Asp Tyr
210                 215                 220

Pro Lys Val Tyr Leu Lys Gly Ser Ile Leu Ile Met Tyr Thr Gly Leu
225                 230                 235                 240

Phe Ser Gly Tyr Pro Ala Gln Phe Glu Val Ile Trp Pro Tyr Ile Glu
                245                 250                 255

Pro Val Ile Gln Glu Asn Met Leu Leu Leu Arg Leu Ala Pro Asn Asp
            260                 265                 270

Cys Asn Gln Ser Pro Ile Leu Gln Gly Tyr Asn Asn Ser Ile Met Ala
        275                 280                 285

Gly Ile His Val Asp Leu Pro Glu Phe Pro Ala Ser Lys Tyr Ile Phe
290                 295                 300

Gln His Glu Ser Leu Leu Ala Asn Tyr Ser Val Pro Val Ser Thr
305                 310                 315                 320

Pro Lys Phe Pro Arg Tyr Met Tyr His Gly Gly Ser Asp Glu Leu Ala
                325                 330                 335

Lys Leu Ser Leu Val Glu Gln Tyr Val Asp Gln Gln Trp Asn Thr Gly
            340                 345                 350

Ala Asn Leu Thr Phe Val Val Tyr Pro Gly Leu Leu His Asp Glu Thr
        355                 360                 365

Ala Tyr Arg Gly Phe Asp Ala Ala Met Asp Trp Leu Asp Ala Gln Leu
370                 375                 380

Asp Ser Gly Tyr Leu Pro Pro Val Asn Ser Thr His Thr Val Asp His
385                 390                 395                 400
```

His His His His His
            405

<210> SEQ ID NO 34
<211> LENGTH: 20
<212> TYPE: DNA
<213> ORGANISM: Artificial sequence
<220> FEATURE:
<223> OTHER INFORMATION: Primer

<400> SEQUENCE: 34
ccatactcaa gcgcgaacac                                                   20

<210> SEQ ID NO 35
<211> LENGTH: 26
<212> TYPE: DNA
<213> ORGANISM: Artificial sequence
<220> FEATURE:
<223> OTHER INFORMATION: Primer

<400> SEQUENCE: 35
gagctcaaga cgcgtttact caatgc                                            26

<210> SEQ ID NO 36
<211> LENGTH: 21
<212> TYPE: DNA
<213> ORGANISM: Artificial sequence
<220> FEATURE:
<223> OTHER INFORMATION: Primer

<400> SEQUENCE: 36
cgtcgactgt atgagttgag t                                                 21

<210> SEQ ID NO 37
<211> LENGTH: 22
<212> TYPE: DNA
<213> ORGANISM: Artificial sequence
<220> FEATURE:
<223> OTHER INFORMATION: Primer

<400> SEQUENCE: 37
gctgcaggac tccctttagg cc                                                22

<210> SEQ ID NO 38
<211> LENGTH: 12
<212> TYPE: PRT
<213> ORGANISM: Candida bombicola

<400> SEQUENCE: 38

Ala Gly Leu Pro Leu Gly Tyr Thr Ala Ala Pro Ala
1               5                   10

<210> SEQ ID NO 39
<211> LENGTH: 11
<212> TYPE: PRT
<213> ORGANISM: Candida bombicola

<400> SEQUENCE: 39

Lys Val Val Gln Val Ala Tyr Lys Thr Arg Leu
1               5                   10

<210> SEQ ID NO 40
<211> LENGTH: 16
<212> TYPE: PRT
<213> ORGANISM: Candida bombicola

<400> SEQUENCE: 40

Arg Gln Glu Gly Tyr Ala Gly Leu Asp Gly Ile Arg Ala Ala Arg Asn
1               5                   10                  15

<210> SEQ ID NO 41
<211> LENGTH: 18
<212> TYPE: PRT
<213> ORGANISM: Candida bombicola

<400> SEQUENCE: 41

Lys Ser Ser Asn Tyr Leu Pro Val Thr Ser Asn Leu Ser Ala Ile Ser
1               5                   10                  15

Arg Glu

<210> SEQ ID NO 42
<211> LENGTH: 19
<212> TYPE: PRT
<213> ORGANISM: Candida bombicola

<400> SEQUENCE: 42

Arg Leu Thr Asp Gly Asn Asp Ser Phe Ser Ile Ala Ser Ile Phe Ile
1               5                   10                  15

Pro Lys Asn

<210> SEQ ID NO 43
<211> LENGTH: 20
<212> TYPE: PRT
<213> ORGANISM: Candida bombicola

<400> SEQUENCE: 43

Arg His Cys Ile Ile Pro Asp His Glu Gly Tyr Ile Ser Gly Phe Phe
1               5                   10                  15

Ala Gly Arg Gln
            20

<210> SEQ ID NO 44
<211> LENGTH: 6
<212> TYPE: PRT
<213> ORGANISM: Candida bombicola

<400> SEQUENCE: 44

Gly Tyr Ser Gly Gly Ala
1               5

<210> SEQ ID NO 45
<211> LENGTH: 22
<212> TYPE: PRT
<213> ORGANISM: Candida bombicola

<400> SEQUENCE: 45

Lys Gly Arg His Cys Ile Ile Pro Asp His Glu Gly Tyr Ile Ser Gly
1               5                   10                  15

Phe Phe Ala Gly Arg Gln
            20

<210> SEQ ID NO 46
<211> LENGTH: 26
<212> TYPE: PRT
<213> ORGANISM: Candida bombicola

<400> SEQUENCE: 46

```
Arg Leu Thr Asp Gly Asn Asp Ser Phe Ser Ile Ala Ser Ile Phe Ile
1               5                   10                  15

Pro Lys Asn Pro Ser Pro Glu Leu Lys Leu
            20              25

<210> SEQ ID NO 47
<211> LENGTH: 26
<212> TYPE: PRT
<213> ORGANISM: Candida bombicola

<400> SEQUENCE: 47

Arg Glu Leu Leu Thr Leu Pro Asp Ile Phe Asp Phe Gly Pro Asn Leu
1               5                   10                  15

Glu Lys Val Val Gln Val Ala Tyr Lys Thr
            20                  25

<210> SEQ ID NO 48
<211> LENGTH: 28
<212> TYPE: PRT
<213> ORGANISM: Candida bombicola

<400> SEQUENCE: 48

Lys Thr Arg Leu Thr Asp Gly Asn Asp Ser Phe Ser Ile Ala Ser Ile
1               5                   10                  15

Phe Ile Pro Lys Asn Pro Ser Pro Glu Leu Lys Leu
            20                  25
```